US010240998B2

(12) United States Patent
Prasad et al.

(10) Patent No.: US 10,240,998 B2
(45) Date of Patent: Mar. 26, 2019

(54) DETERMINING A LOCATION AND SIZE OF A GAS SOURCE WITH A SPECTROMETER GAS MONITOR

(71) Applicants: The United States of America, as represented by the Secretary of Commerce, Washington, DC (US); The Regents of the University of Colorado, a body corporate, Denver, CO (US)

(72) Inventors: Kuldeep Prasad, Vienna, VA (US); Caroline Alden, Boulder, CO (US); Gregory Brian Rieker, Boulder, CO (US); Robert James Wright, Boulder, CO (US); Sean Coburn, Longmont, CO (US)

(73) Assignees: The United States of America, as represented by the Secretary of Commerce, Washington, DC (US); The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/729,079

(22) Filed: Oct. 10, 2017

(65) Prior Publication Data
US 2018/0045596 A1 Feb. 15, 2018

Related U.S. Application Data

(63) Continuation-in-part of application No. 15/152,543, filed on May 11, 2016.
(Continued)

(51) Int. Cl.
G01M 3/16 (2006.01)
G01M 3/20 (2006.01)
(Continued)

(52) U.S. Cl.
CPC ............... *G01M 3/16* (2013.01); *G01J 3/42* (2013.01); *G01M 3/202* (2013.01); *G01M 3/22* (2013.01)

(58) Field of Classification Search
CPC ............ G01J 3/42; G01M 3/202; G01W 1/00
See application file for complete search history.

(56) References Cited

U.S. PATENT DOCUMENTS

| 6,873,267 B1 * | 3/2005 | Tubel | E21B 43/12 |
| | | | 166/250.15 |
| 8,595,020 B2 | 11/2013 | Marino | |
| 2013/0282292 A1 * | 10/2013 | Wang | G01V 1/364 |
| | | | 702/17 |

OTHER PUBLICATIONS

Ram Hashmonay, et al., Computed tomography of air pollutants using radial scanning path-integrated optical remote sensing, Atmospheric Environment, Apr. 3, 1998, p. 267-274, 33.
(Continued)

*Primary Examiner* — Elias Desta
(74) *Attorney, Agent, or Firm* — Lathrop Gage LLP

(57) ABSTRACT

A process for determining a location and size of a gas source within an area with a spectrometer gas monitor includes: providing the spectrometer gas monitor; performing fence line monitoring of the area with the spectrometer gas monitor; collecting spectroscopic data over multiple open paths around the area with the spectrometer gas monitor; measuring atmospheric conditions along gas inflows and gas outflows of the area; subtracting a background for a selected gas from the spectroscopic data; applying a boundary constraint to the spectroscopic data; determining an atmospheric concentration of air entering the area; applying bootstrapping to the spectroscopic data; applying zero minimum elimination to the spectroscopic data; and producing inversion data from the spectroscopic data to determine the location and size of the gas source within the area.

17 Claims, 19 Drawing Sheets

Related U.S. Application Data

(60) Provisional application No. 62/160,163, filed on May 12, 2015, provisional application No. 62/409,569, filed on Oct. 18, 2016.

(51) Int. Cl.
  *G01M 3/22* (2006.01)
  *G01J 3/42* (2006.01)

(56) References Cited

OTHER PUBLICATIONS

Thomas Flesch, et al., Estimating gas emissions from a farm with an inverse-dispersion technique, Atomospheric Environment, Apr. 25, 2005, p. 4863-4874, 39.

Ram Hashmonay, et al., Localizing gaseous fugutive emissions sources by combining real-time optical remote sensing and wind data, Journal of the air & waste management association, Dec. 27, 2011, p. 1374-1379.

Xin Lan, et al., Characterizing fugitive methane emissions in the barnett shale area using a mobile laboratory, Enviromental Science & Technology, Jul. 7, 2015, p. 8139-8146, 49.

Laura Thomson, et al., An improved algorithm for locating a gas source suing inverse methods, Atmospheric Environment, Oct. 3, 2006, p. 1128-1134, 41.

Zachary Levine, et al., The detection of carbon dioxide leaks using quasi-tomographic laser absorption spectroscopy measurements in variable wind, Atmospheric measurement techniques, Apr. 13, 2016, p. 1627-1636.

Israel Lopez-Coto, et al., Tower-based greenhouse gas measurement network design—The National Institute of Standards and Technology North Ease corridor testbed, Advanced in Atmospheric Sciences, 2017, 1095-1105, 34.

Heming Hu, et al., Greenhouse gas emissions and dispersion, National Institute of Standards and Technology Internal Report 8070, Sep. 2015.

U.S. Appl. No. 15/152,543, Notice of Allowance dated Oct. 26, 2018, 9 pp.

\* cited by examiner

DETERMINING A LOCATION AND SIZE OF A GAS SOURCE WITH A SPECTROMETER GAS MONITOR

CROSS REFERENCE TO RELATED APPLICATIONS

This application is a continuation-in-part of U.S. patent application Ser. No. 15/152,543, filed on May 11, 2016, which claims the benefit of U.S. provisional patent application No. 62/160,163, filed on May 12, 2015, the entire contents of which are incorporated herein by reference.

This application also claims the benefit of U.S. Provisional Patent Application Ser. No. 62/409,569, filed on Oct. 18, 2016, the entire content of which is incorporated herein by reference.

STATEMENT REGARDING FEDERALLY SPONSORED RESEARCH

This invention was made with government support under grant number DE-AR0000539 awarded by the U.S. Department of Energy and grant number DE-FE0029168 awarded by the U.S. Department of Energy. The government has certain rights in the invention.

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 17-005US1.

BRIEF DESCRIPTION

Disclosed is a process for determining a location and size of a gas source within an area with a spectrometer gas monitor, the process comprising: providing the spectrometer gas monitor; performing fence line monitoring of the area with the spectrometer gas monitor; collecting spectroscopic data over multiple open paths around the area with the spectrometer gas monitor; measuring atmospheric conditions along gas inflows and gas outflows of the area; subtracting a background for a selected gas from the spectroscopic data; applying a boundary constraint to the spectroscopic data; determining an atmospheric concentration of air entering the area; applying bootstrapping to the spectroscopic data; applying zero minimum elimination to the spectroscopic data; and producing inversion data from the spectroscopic data to determine the location and size of the gas source within the area.

Further disclosed is a computer-implemented method, comprising: providing the spectrometer gas monitor; performing fence line monitoring of the area with the spectrometer gas monitor; collecting spectroscopic data over multiple open paths around the area with the spectrometer gas monitor; measuring atmospheric conditions along gas inflows and gas outflows of the area; subtracting a background for a selected gas from the spectroscopic data; applying a boundary constraint to the spectroscopic data; determining an atmospheric concentration of air entering the area; applying bootstrapping to the spectroscopic data; applying zero minimum elimination to the spectroscopic data; and producing inversion data from the spectroscopic data to determine the location and size of the gas source within the area.

Disclosed also is a system comprising: one or more computers configured to perform operations, the operations comprising: providing the spectrometer gas monitor; performing fence line monitoring of the area with the spectrometer gas monitor; collecting spectroscopic data over multiple open paths around the area with the spectrometer gas monitor; measuring atmospheric conditions along gas inflows and gas outflows of the area; subtracting a background for a selected gas from the spectroscopic data; applying a boundary constraint to the spectroscopic data; determining an atmospheric concentration of air entering the area; applying bootstrapping to the spectroscopic data; applying zero minimum elimination to the spectroscopic data; and producing inversion data from the spectroscopic data to determine the location and size of the gas source within the area.

Also disclosed is a computer-readable medium having instructions stored thereon, which, when executed by a processor, cause the processor to perform operations comprising: providing the spectrometer gas monitor; performing fence line monitoring of the area with the spectrometer gas monitor; collecting spectroscopic data over multiple open paths around the area with the spectrometer gas monitor; measuring atmospheric conditions along gas inflows and gas outflows of the area; subtracting a background for a selected gas from the spectroscopic data; applying a boundary constraint to the spectroscopic data; determining an atmospheric concentration of air entering the area; applying bootstrapping to the spectroscopic data; applying zero minimum elimination to the spectroscopic data; and producing inversion data from the spectroscopic data to determine the location and size of the gas source within the area.

BRIEF DESCRIPTION OF THE DRAWINGS

The following descriptions should not be considered limiting in any way. With reference to the accompanying drawings, like elements are numbered alike.

FIG. 1 shows a spectrometer gas monitor for determining a location and size of a gas source within an area with;

DETAILED DESCRIPTION

Figure 1:
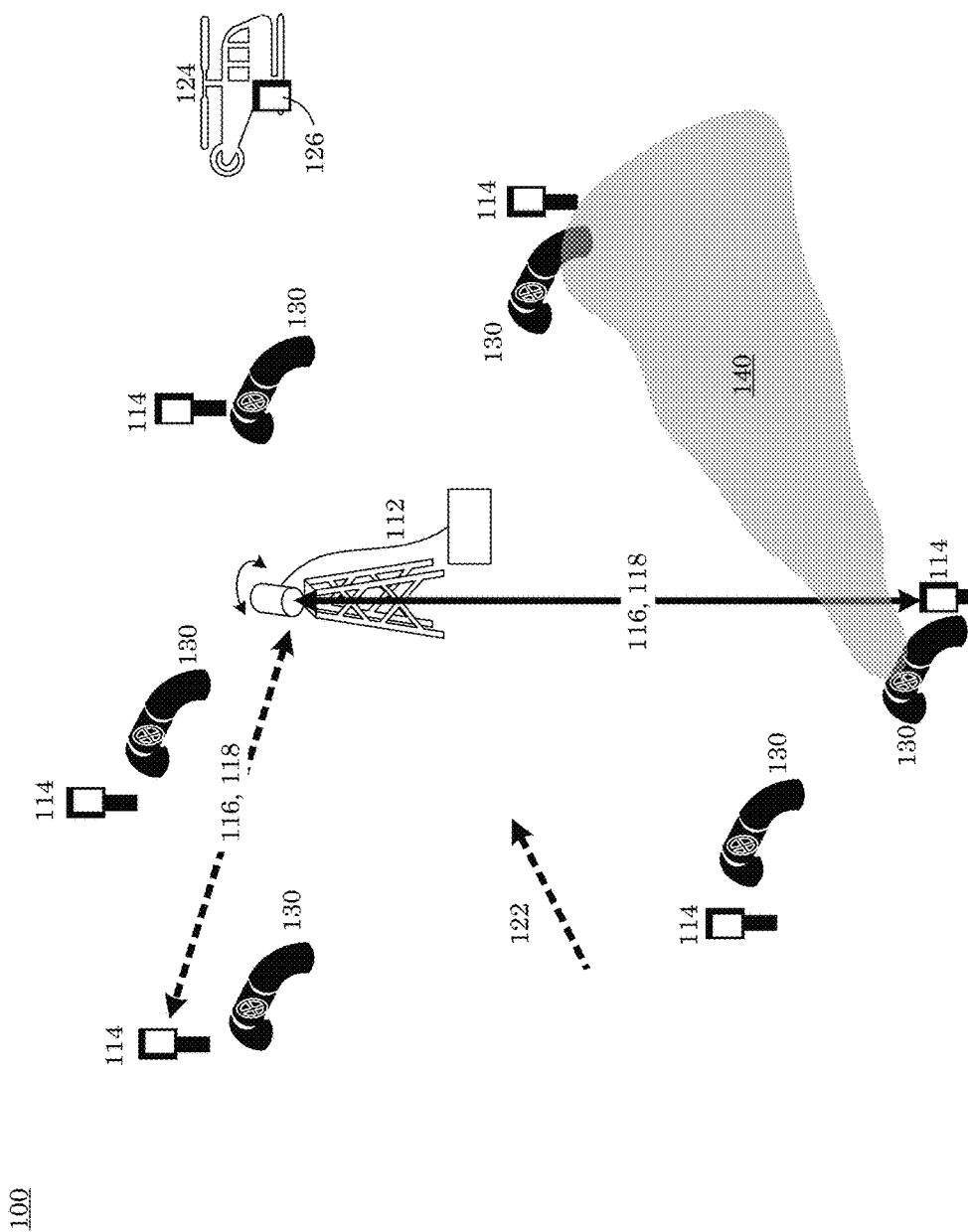

A detailed description of one or more embodiments is presented herein by way of exemplification and not limitation.

Advantageously and unexpectedly, it has been discovered that a gas spectrometer monitor and processes herein provide determination of a location and size of a gas source within an area. Moreover, the gas spectrometer monitor can determine a flux of a gas from the gas source in the area that can be, e.g., from tens to thousands of meters. Further, the spectrometer gas monitor provides statistical certainty of the location and size of the gas, temporally continuous monitoring of gases, and quantification of background gas conditions.

The gas spectrometer monitor includes frequency combs lasers, whose output consists of hundreds or thousands of individual wavelengths. Frequency comb spectroscopy provides accurate measurement of $CH_4$, $^{13}CH_4$, $H_2O$, and other species as well as temperature and pressure. Since no instrument distortion occurs, and the frequency combs have a near perfect wavelength axis, the frequency combs are drift-free and calibration-free. The gas spectrometer monitor also provides biogenic or thermogenic differentiation through measurements of isotope ratios of methane and speciation through propane or ethane measurement.

In an embodiment, with reference to FIG. 1, FIG. 2, FIG. 3, FIG. 4, FIG. 5, and FIG. 6, spectrometer gas monitor 100 includes spectrometer 112 that includes a light source and detector in which the light source provides source light 116 that propagates in area 110 as a plurality of open-path beams; a plurality of retroreflectors in optical communication with light source 112 and that receives source light 116 and reflects source light 116 as reflected light 118; and a detector that detects reflected light 118. Light source 112 communicates source light 116 and receives reflected light 118 from a variety of directions to detect gas 140 from gas sources 130. In this manner, spectrometer gas monitor 100 scans area 110 with source light 116 over open beam paths and detects reflected light 118 from retroreflectors 114. Accordingly, spectroscopic data can be acquired continuously during a period of days under various weather conditions.

Figure 2:
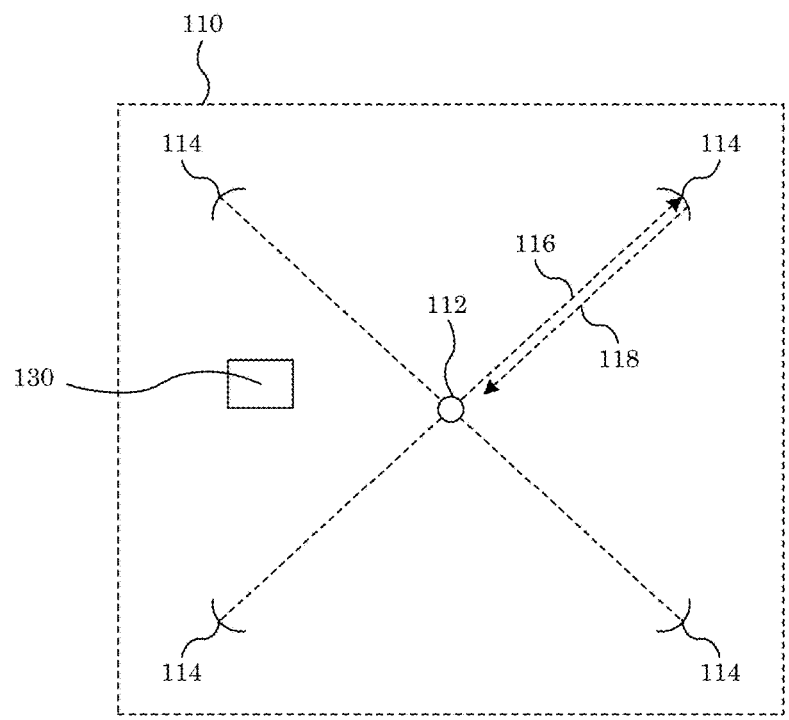
FIG. 2 shows a spectrometer gas monitor for determining a location and size of a gas source within an area with a spectrometer gas monitor.
Figure 5:
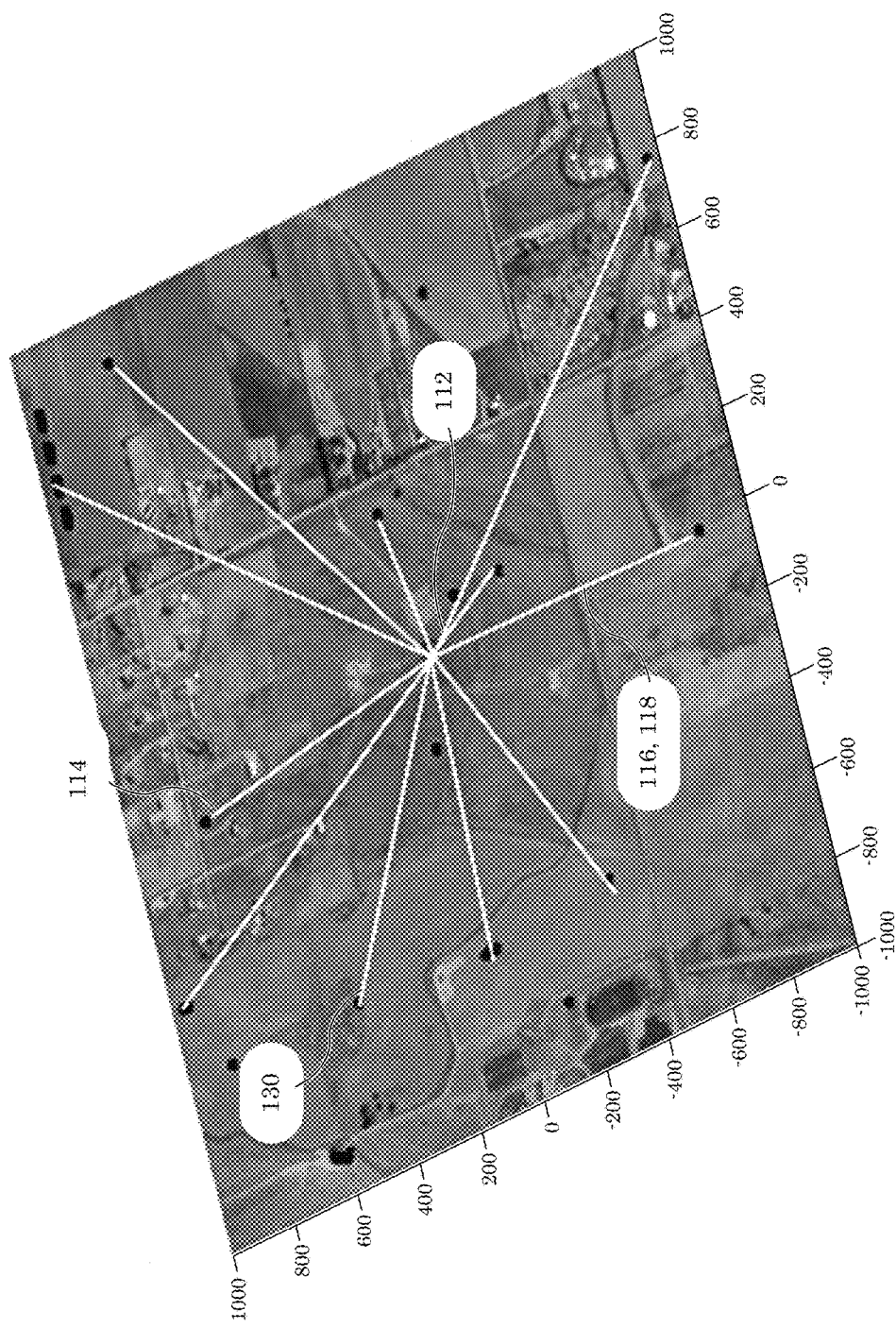
FIG. 5 shows a spectrometer gas monitor for determining a location and size of a gas source within an area with a spectrometer gas monitor.

FIG. 1, FIG. 2, and FIG. 5 show spectrometer 112 disposed among retroreflectors 114 and in area 110. In an embodiment, with reference to FIG. 3 and FIG. 4, spectrometer 112 is disposed outside of area 110. It should be appreciated that retroreflectors 114 provide a fence line that encapsulates area 110 in a team umbrella that includes open-path beams of source light 116. Accordingly, any gas that flows into her out of area 110 can be subjected to radiation by source light 116. Since retroreflectors 114 reflects source light 116 as reflected light 118 to spectrometer 112, the detector of spectrometer 112 can detect a difference in source light 116 and reflected light 118 due to absorption of source light 116 or reflected light 118 by the gas. It is contemplated that. 110 can include gas source 130, wherein gas source 130 is an origin of gas 140. Moreover, wind 122 can be a meteorological factor that affects gas 140 inside or outside of area 110.

Figure 3:
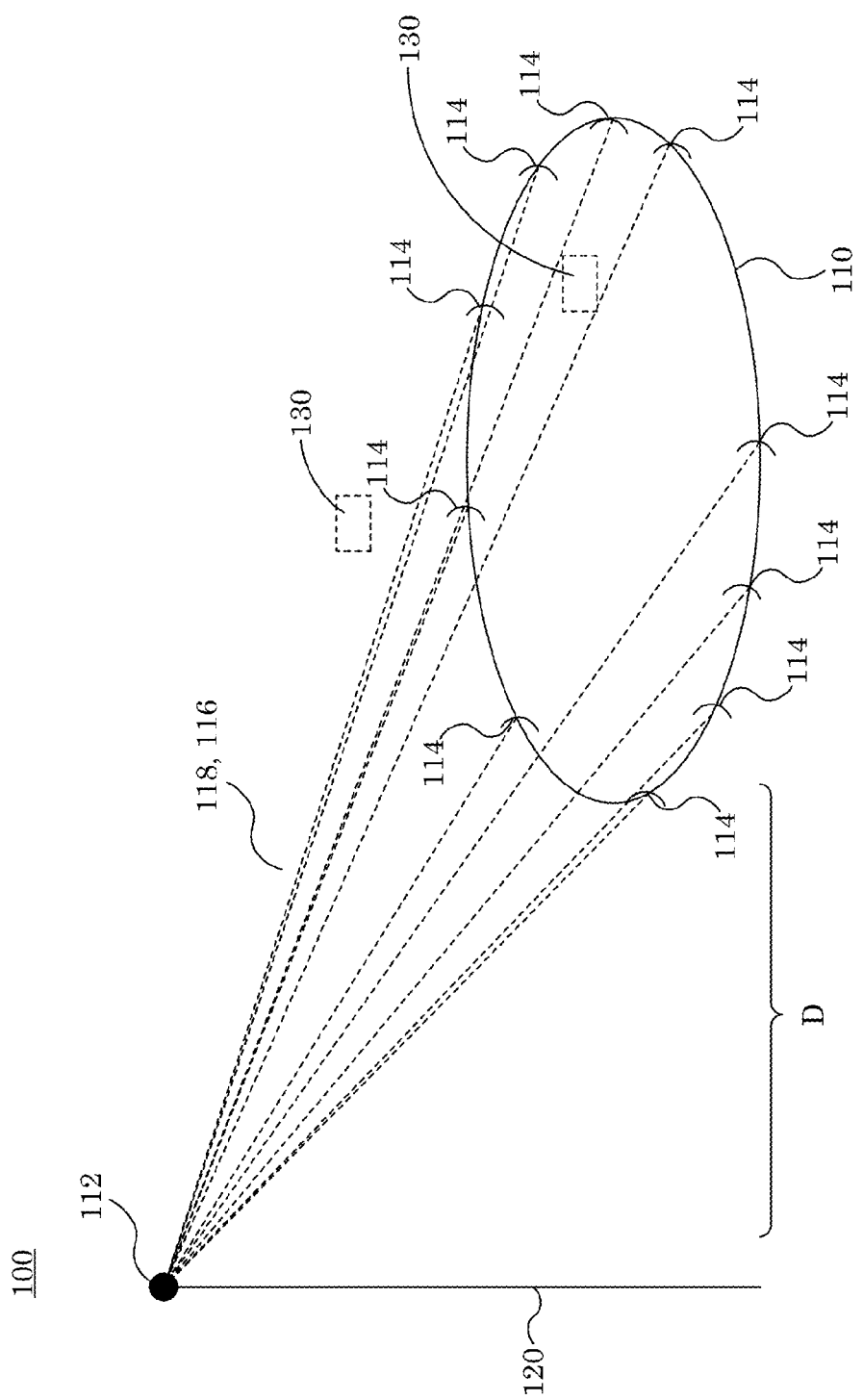
FIG. 3 shows a spectrometer gas monitor for determining a location and size of a gas source within an area with a spectrometer gas monitor.
Figure 4:
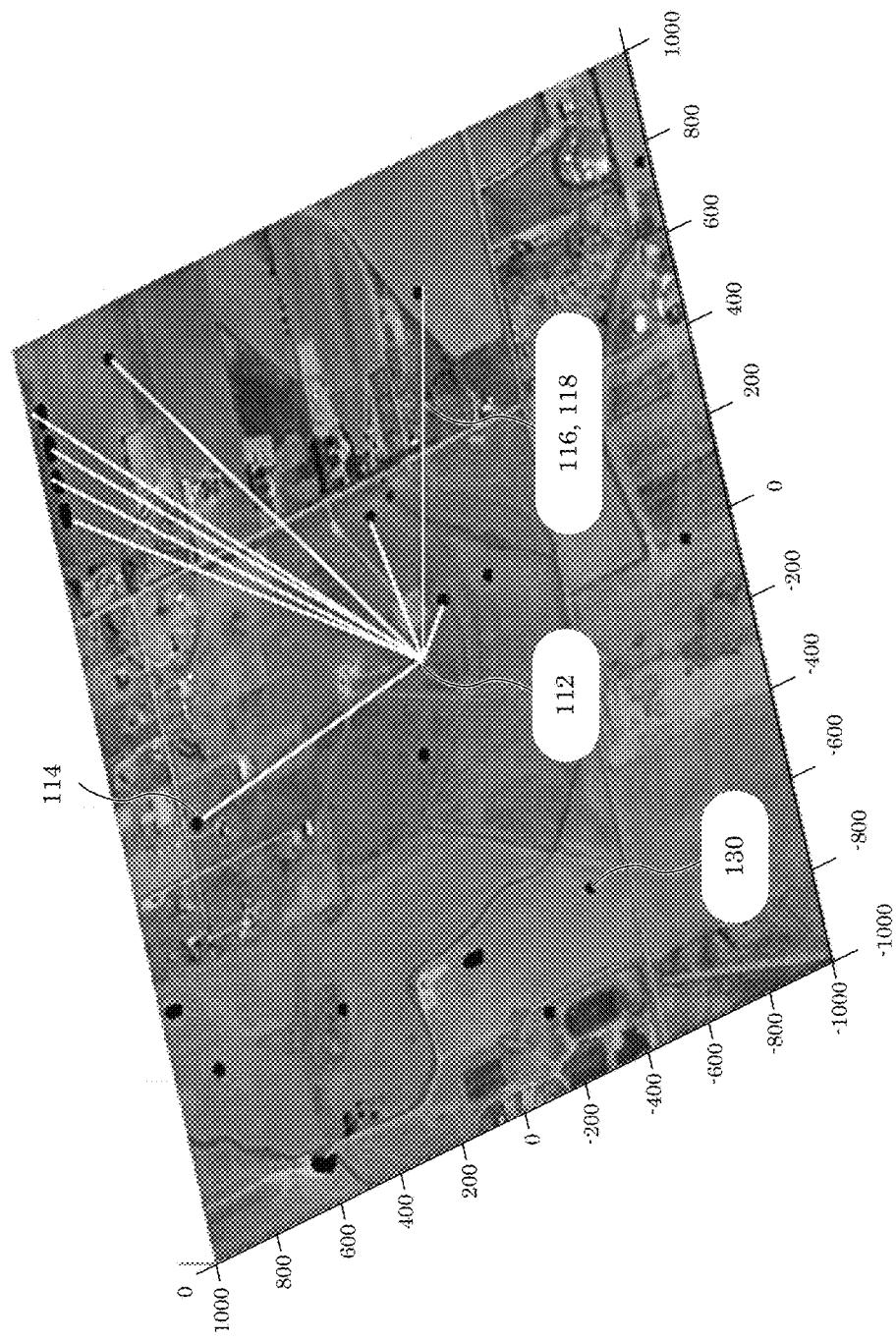
FIG. 4 shows a spectrometer gas monitor for determining a location and size of a gas source within an area with a spectrometer gas monitor.

In an embodiment, spectrometer 112 can be disposed on a pole 120 or other structure for elevation of spectrometer 112 above a ground plane of area 110. With reference to FIG. 3, spectrometer 112 on pole 120 can be distance D from proximate retroreflector 114. Distance D can be selected based on various characteristics of spectrometer 112, area 110, weather conditions, and the like.

In some embodiments, retroreflectors 114 reflect source light 116 as reflected light 118 directly back to spectrometer 112. Retroreflectors 114 can provide a high degree of pointing flexibility, e.g., beams from a large array of incoming angles can be re-directed back the direction from which they came. As such, alignment of retroreflectors 114 with respect to spectrometer 112 can be automatic, and spectrometer 112 can be configured to track retroreflector 114.

Retroreflectors 114 can be located on a well platform, riser, tower, tree, fence, and the like. Alternative reflectors to retroreflectors 114 can be used, including other fixed reflectors or environmental reflectors such as buildings. In some embodiments, and unmanned aerial vehicle (UAV) 212 with reflector 126 periodically flies a path around area 110 and source light 116 is reflected as reflected light 118 off of reflector 126 in various directions covering area 110 containing gas source 130 (e.g., a well, well pad, and the like).

Figure 6:
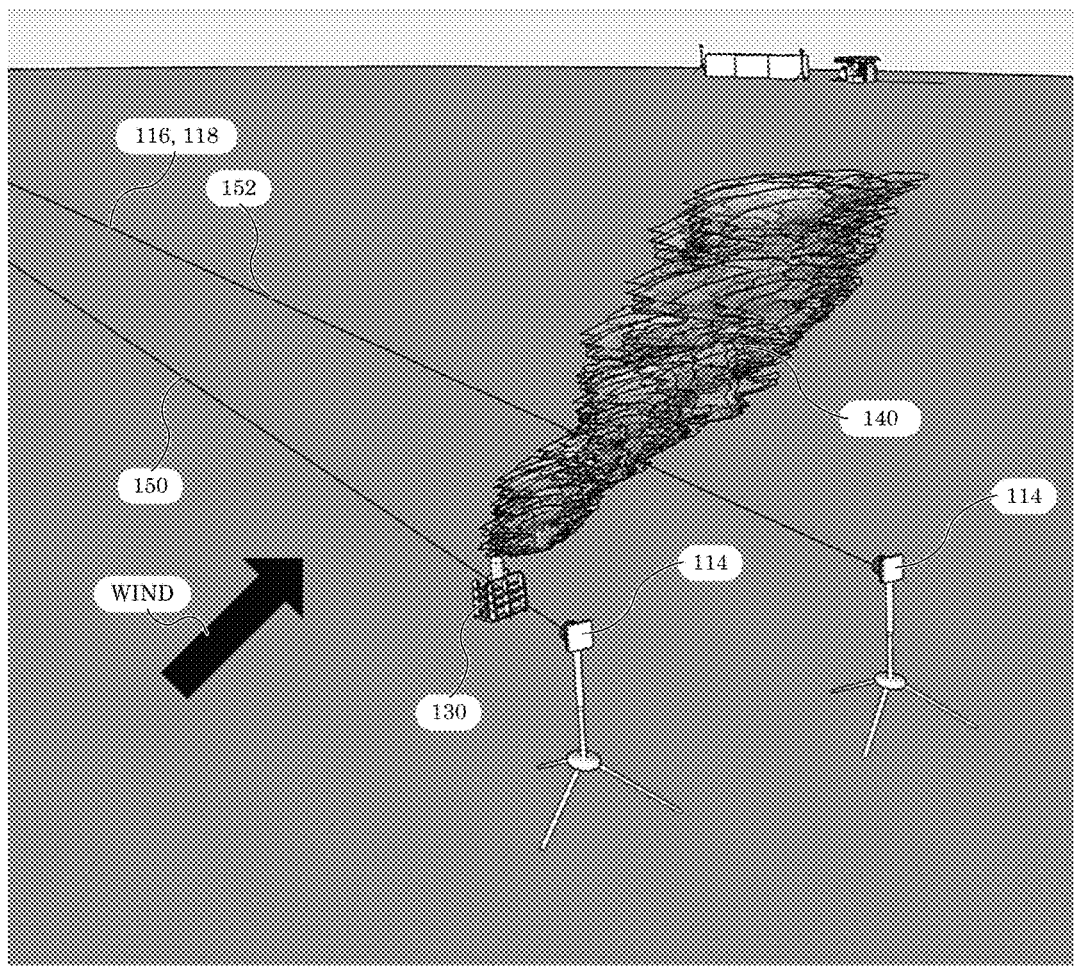
FIG. 6 shows a determination of a location and size of a gas source within an area with a spectrometer gas monitor that includes orthogonal sampling.

In an embodiment, with reference to FIG. 6, gas spectrometer monitor 100 is configured to perform orthogonal beam sampling. Here, a pair of retroreflectors (114) of spectrometer gas monitor 100 are disposed relative to gas source 130 such that gas source 130 is interposed between retroreflectors 114. In this manner, source light 116 and reflected light 118 occur on both sides of gas source 130 so that gas 140 travels orthogonally through downwind beam 152 (that includes second source light 116 and second reflected light 118), but gas 140 is absent in the wind beam 150 (that includes first source light 116 and first reflected light 118). Accordingly, downwind beam 152 has different spectroscopic data and then as upwind beam 150. Moreover, second source light 116 in downwind beam 152 has different spectroscopic data and then second reflected light 118 in downwind beam 152.

Figure 7:
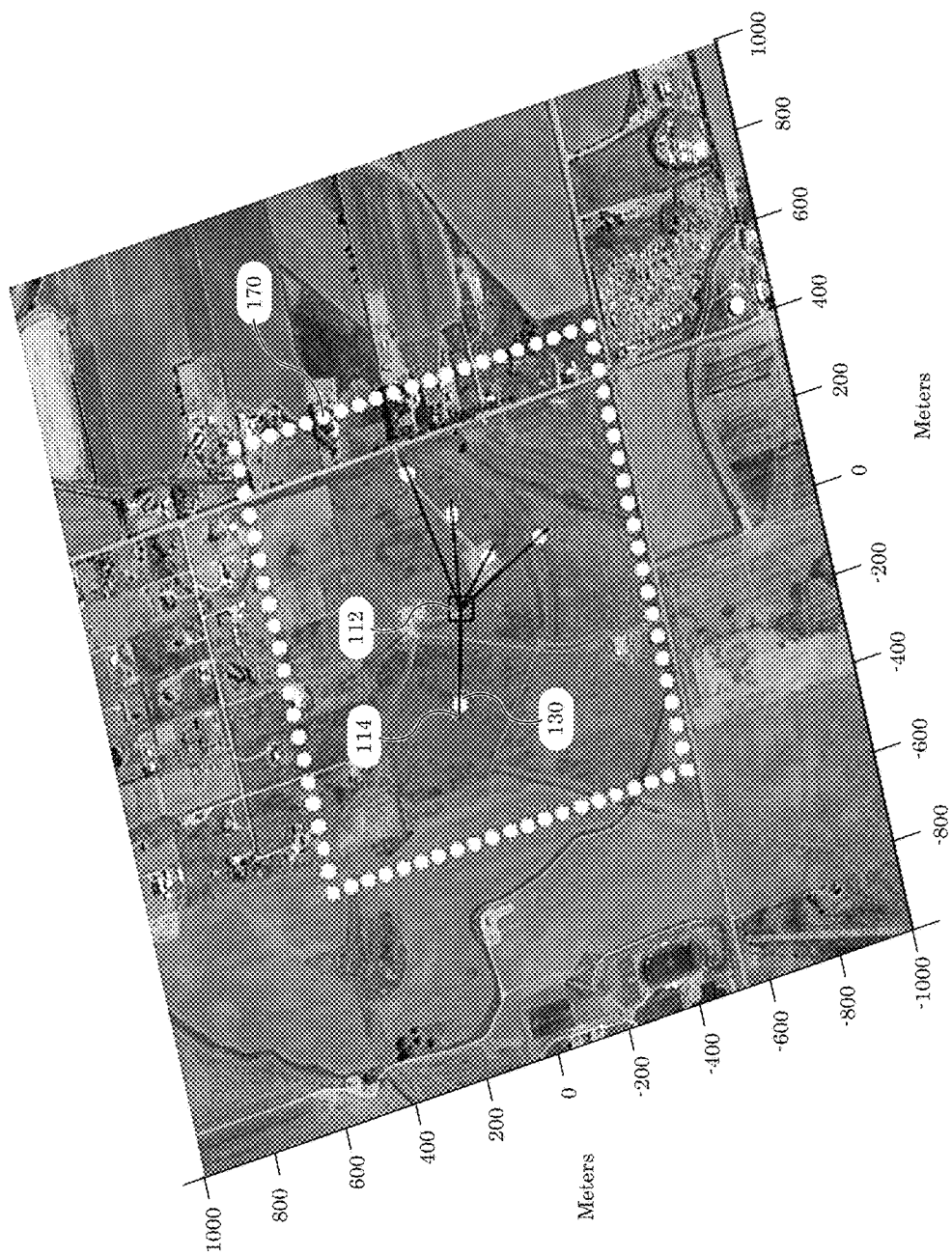
FIG. 7 shows a spectrometer gas monitor that includes priors for determining a location and size of a gas source within an area.

According to an embodiment, with reference to FIG. 7, gas spectrometer monitor 100 includes a plurality of priors 170 disposed along a perimeter of area 110. Priors 170 can include potential leak locations in the domain of interest. These priors allow us to account for background variability in methane and background sources.

Figure 8:
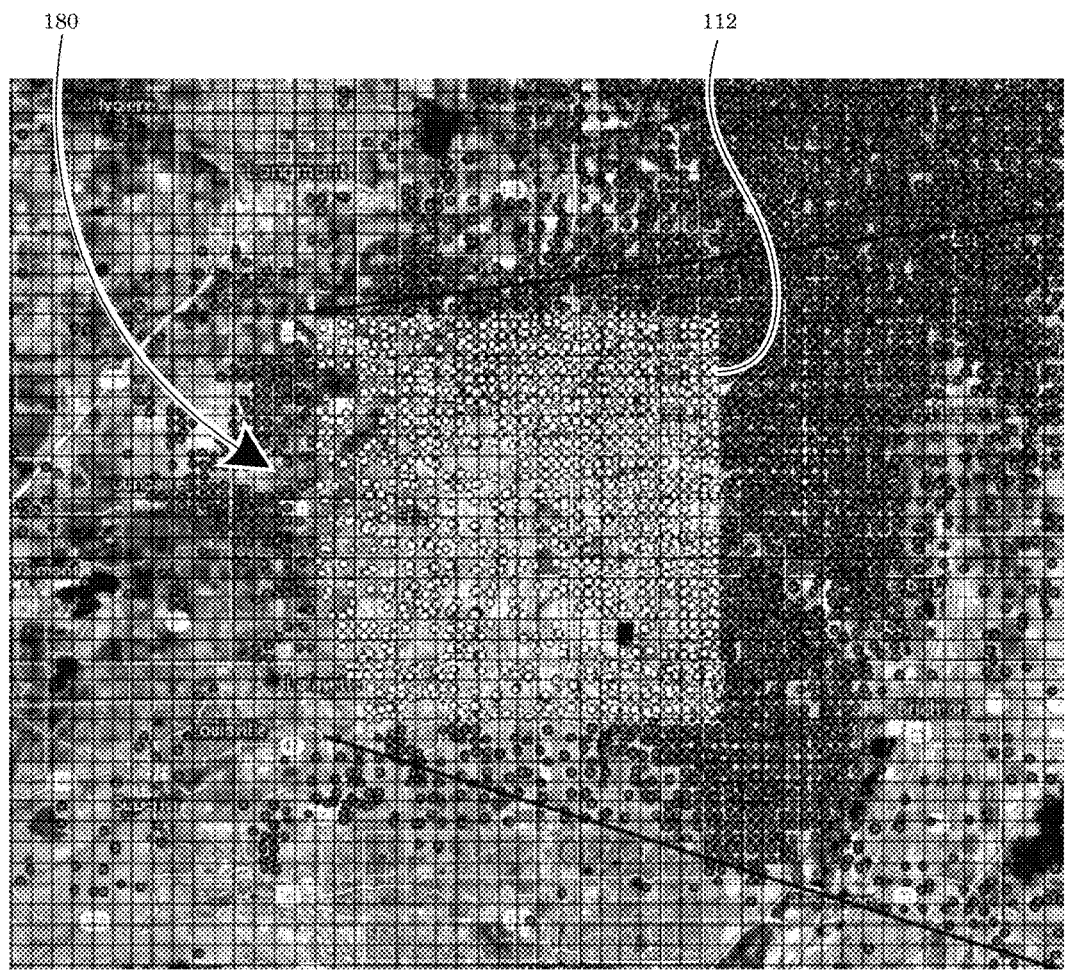
FIG. 8 shows spectrometer gas monitors in a cluster for determining a location and size of a gas source within an area.
Figure 9:
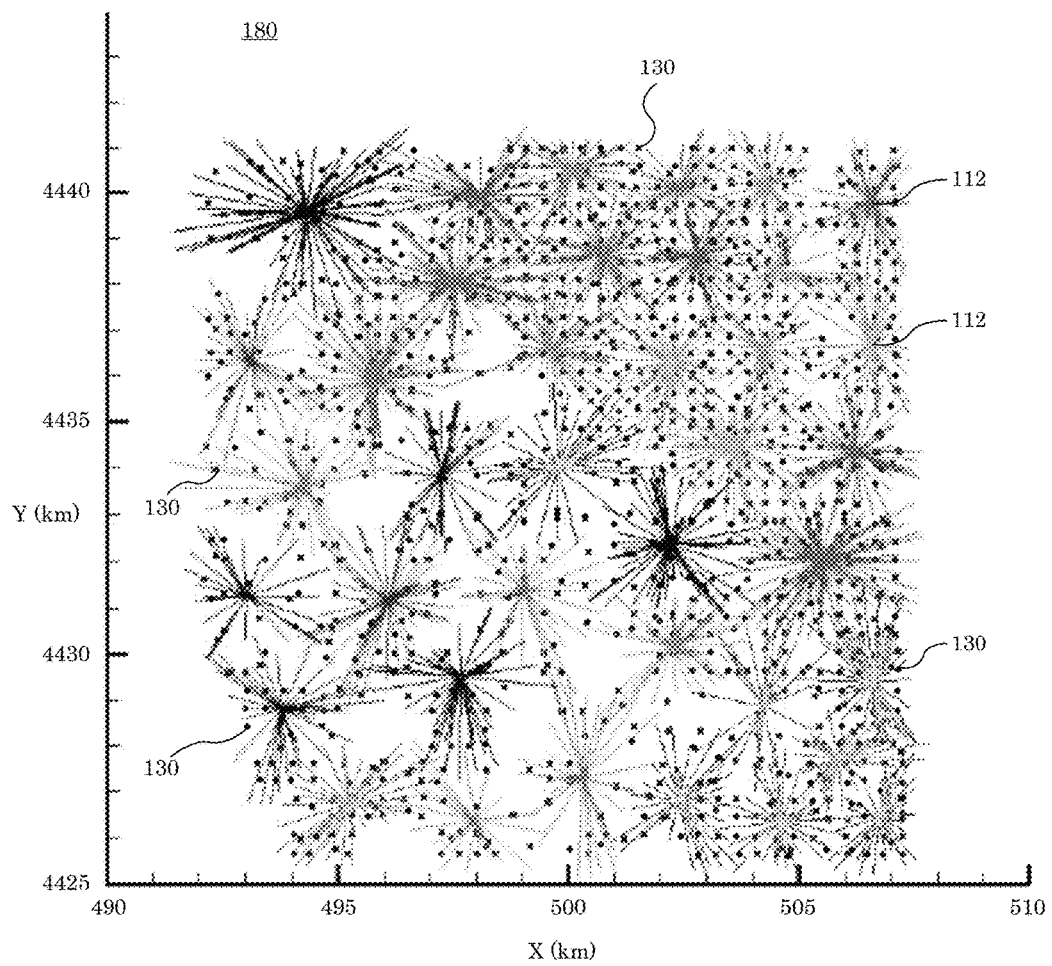
FIG. 9 shows a zoomed view of the spectrometer gas monitors in the cluster shown in FIG. 8.

In an embodiment, with reference to FIG. 8 and FIG. 9, gas spectrometer monitor 100 includes a plurality of gas sources 130; a plurality of gas spectrometer monitors 100 disposed as cluster 180 in which adjacent spectrometers 112 monitor gas 140 for gas sources 130 across area 110.

Figure 10:
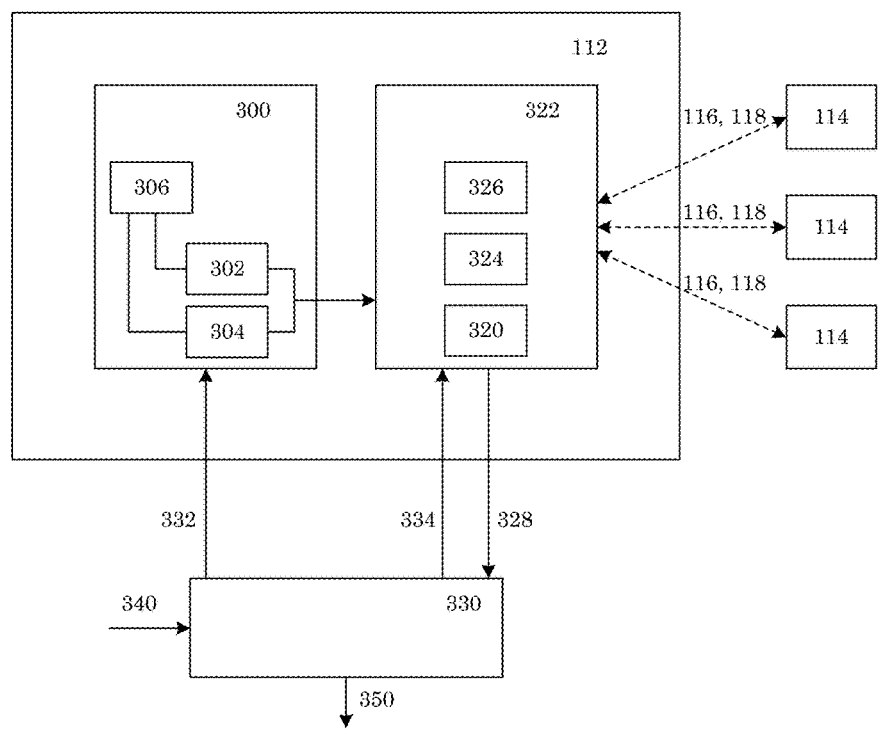
FIG. 10 shows a spectrometer gas monitor for determining a location and size of a gas source within an area.

In an embodiment, with reference to FIG. 10, gas spectrometer monitor 100 includes processor 330 in communication with spectrometer 112. Process 330 combines spectroscopic data from reflected light 118 with meteorological data 340 (such as a direction and speed of wind 122) of area 110 to determine the location of gas source 130. According to an embodiment, processor 330 combines spectroscopic data from reflected light 118 with high-resolution computational fluid dynamics and inversion techniques to locate and size gas 140 from gas source 130.

In an embodiment, spectrometer 112 sends source light 116 sequentially over different long open paths to retroreflectors 114. The measured absorption spectra from reflected light 118 are fit to determine a concentration enhancement of gas 140 (e.g., a hydrocarbon such as methane). High resolution large eddy simulation-based inversion techniques can be used to interpret the measured enhancement into methane leak size and location of gas source 130. A sensitivity of spectrometer 112 provides detection of small leaks of gas 140 over a range of heights and downwind distances so that a location of retroreflectors 114 is flexible. Measurement of gas 140 from gas source 130 is accurate, sensitive, calibration and drift-free.

In an embodiment, with reference to FIG. 10, gas spectrometer monitor 100 includes processor 330 in communication with spectrometer 112. Here, spectrometer 212 communicates source light 116 via transmitter/receiver 322 to retroreflectors 114, receives reflected light 118 from retroreflectors 114, and detects reflected light 118. Processor 330 combines spectroscopic data 328 from reflected light 118 with meteorological data 340 to detect and locate gas 140 from gas source 130. Meteorological data 340 is involved in modeling plume shape or path of gas 140 from gas source 130.

Figure 11:
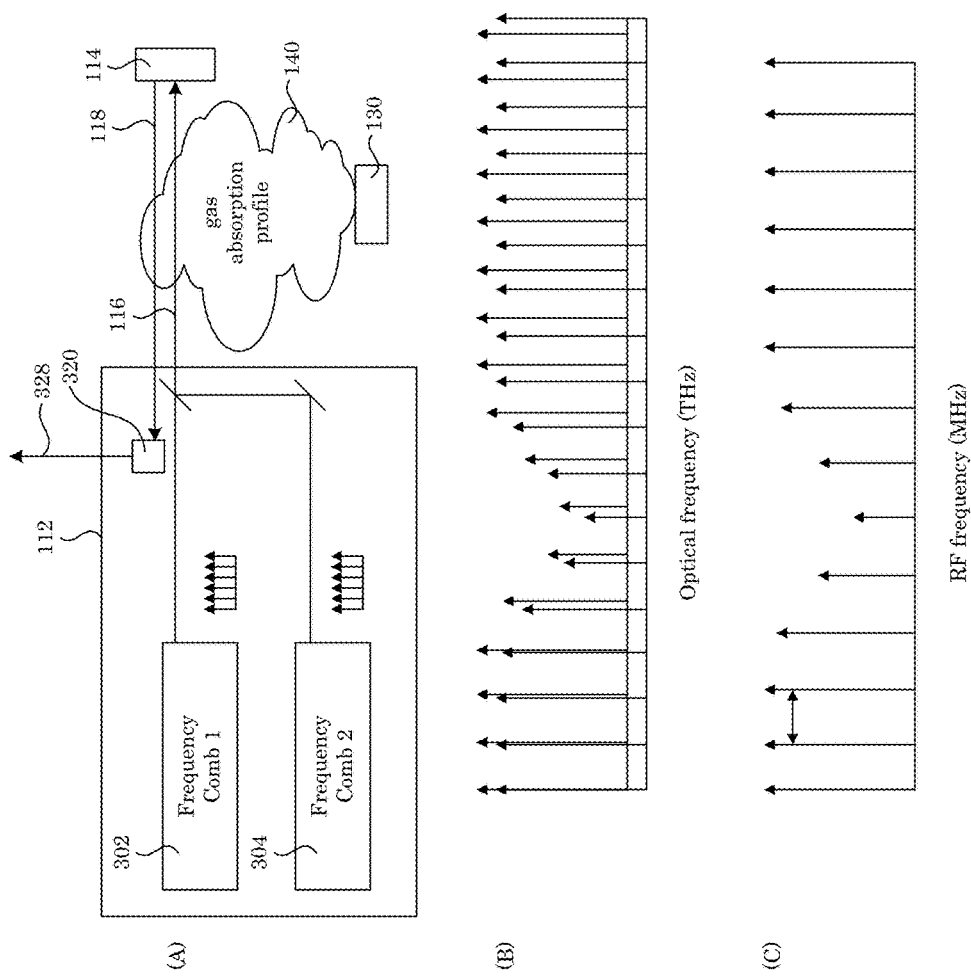
FIG. 11 shows a light source in panel A, source light source in panel B, and reflected light in panel C.

Spectrometer 112 includes light source 300. An exemplary light source 300 is a dual comb source that includes first frequency comb 302 and second frequency comb 304 as shown in FIG. 11A. Operation of light source 300 for dual comb spectroscopy (DCS) provides detection of gas 140 from gas source 130. First frequency comb 302 and second frequency comb 304 (e.g. near infrared light) have slightly different tooth spacing that are combined as source light 116 that passes through gas 140. Source light 116 retroreflectors from retroreflector 114 as reflected light 118 that is received by detector 320 of spectrometer 112. FIG. 11B shows the two frequency combs (302, 304) after the comb light (116 or 118) passes through gas 140 so that some light frequencies have been absorbed by gas 140. FIG. 11C shows a resulting heterodyne interference signal of first frequency comb 302 and second frequency comb 304 in reflected light 118 at detector 320, e.g., at radiofrequency (RF) frequencies.

It should be appreciated that DCS provided by spectrometer 112 overcomes limitations of single or sparse wavelength absorption or LIDAR approaches. Namely, DCS enables accurate correction of baseline laser intensity of frequency combs (302, 304) and simultaneous measurement of hydrocarbon such as $CH_4$, $^{13}CH_4$, ethane, acetylene, and the like as well as hydrocarbon species such as water and conditions such as temperature, pressure, and the like. Moreover, spectrometer 112 provides interference-free, true dry-air mole fractions that account for variable water vapor dilution. Without instrument distortion, e.g., of line shape, and a near perfect wavelength axis, the spectroscopic absorption technique provided by gas spectrometer monitor 100 is drift-free and requires no calibration. Compared with single point measurements that might be deployed on a tower or a mobile platform (e.g., aircraft, vehicle, and the like), get spectrometer monitor 100 requires no operator involvement and can interrogate multiple locations simultaneously.

Again, with reference to FIG. 10, spectrometer 112 includes comb units (302, 304) and stabilizer circuitry 306 to stabilize generated comb combination 308 or to electronically post-correct the spectroscopic data 328. Combs 308 are provided to transmitter/receiver unit 322 including telescope 326 for transmitting source light 116 and receiving reflected light 118, gimbal 324 to scan beams of source light 116 over area 110, and detector 320 to detect reflected light 118 from retroreflectors 114 and provide spectroscopic data 328 to processor 330.

Processor 330 provides control signals (332, 334) to light source 300 and transmitter/receiver unit 322. Process 330 also receives spectroscopic data 328 from detector 320 and meteorological data 340. Processor 330 outputs 350 the location of gas source 130 from which gas 1450 originates in area 130.

Meteorological data 340 can include local measurements of wind 122, temperature, humidity, and the like. Meteorological data 340 can be simulated for area 110, e.g., from models such as the Weather Research and Forecasting (WRF) Model.

The frequency comb spectrometer provides low cost and high performance. The frequency combs can be assembled from telecommunications fiber and telecom components that have a selected mean time between failures of more than 200,000 hours. An optics package of the frequency comb spectrometer can be, e.g., 0.7 liters. Frequency comb control electronics can include a field programmable gate array (FPGA) and can be similarly small.

In an embodiment, a process for making gas spectrometer monitor 100 includes providing the frequency combs; and disposing the retroreflectors at selected location.

Figure 12:
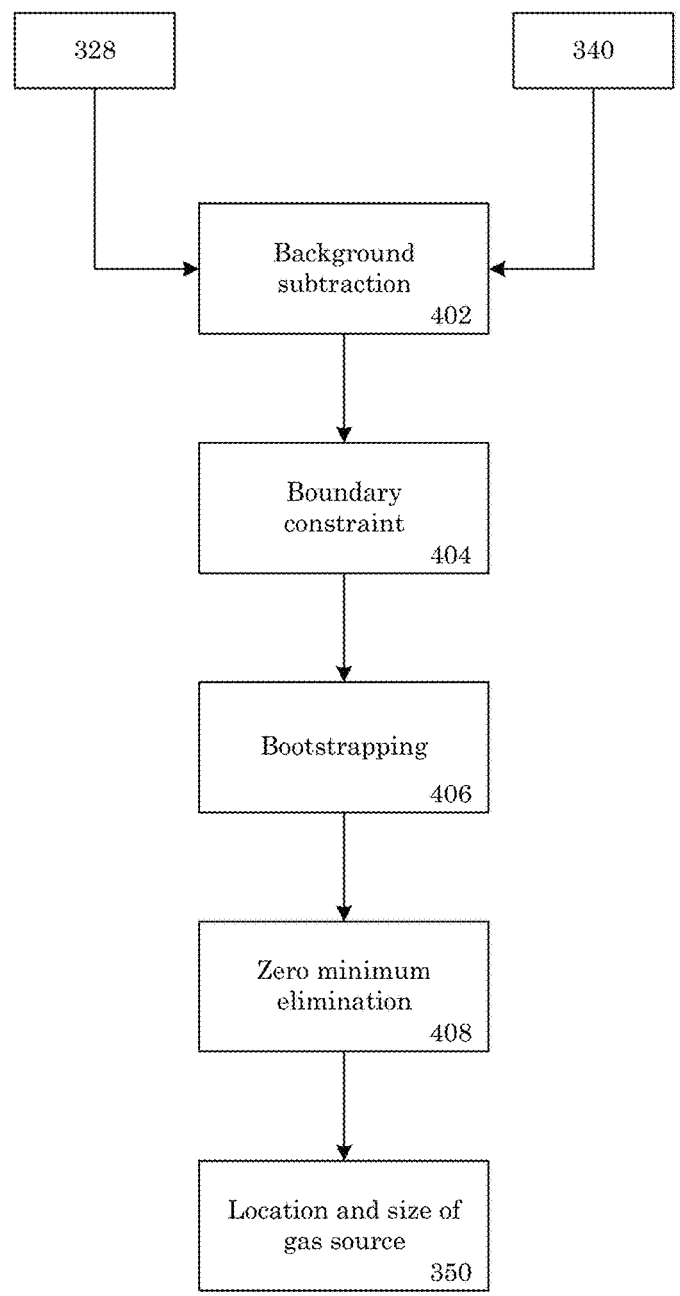
FIG. 12 shows determination of a location size of a gas source.

According to an embodiment, with reference to FIG. 12, a process for determining a location and size of gas source 130 within area 110 with spectrometer gas monitor 100 includes: providing spectrometer gas monitor 100; performing fence line monitoring of area 110 with spectrometer gas monitor 100; collecting spectroscopic data 328 over multiple open paths around area 110 with spectrometer gas monitor 100; measuring atmospheric conditions along gas inflows and gas outflows of area 110; subtracting a background for gas 140 from spectroscopic data 328 (step 402); applying a boundary constraint to spectroscopic data 328 (step 404); determining an atmospheric concentration of air entering area 110; applying bootstrapping to spectroscopic data 328 (step 406); applying zero minimum elimination to spectroscopic data 328 (step 408); and producing inversion data from spectroscopic data 328 to determine the location and size of gas source 130 within area 110 (step 350). Spectrometer gas monitor 100 can include light source 300 that provides source light 116 that propagates in area 110 as a plurality of open-path beams; a plurality of retroreflectors 114 in optical communication with light source 300 and that receives source light 116 and reflects source light 116 as reflected light 118; and detector 320 that detects reflected light 118. Source light 116 can include a source frequency comb that includes comb teeth that include a first intensity, and reflected light 118 that includes a reflected frequency comb that includes the first comb teeth that include a second intensity such that a difference in intensity of the first intensity and the second intensity occurs due to absorption of source light 116 by gas 140.

The process further can include arranging a plurality of spectrometer gas monitors 100 by clustering when area 110 is larger than 1 km$^2$. In an embodiment, the process includes performing orthogonal beam sampling to constrain atmospheric conditions upwind and downwind of area 110.

In the process, performing fence line monitoring includes disposing the spectrometer on a tower at an elevation of 20-25 m above the ground. Retro-reflectors are placed on the perimeter or the fence line of the facility. The combination of spectrometer and retro-reflectors forms an umbrella around the facility and enables us to monitor the flux of tracer gases from the facility. Moreover, fence line monitoring can include encapsulating area 110 with a beam umbrella including open-path beams that includes source light 116 from spectrometer gas monitor 100, wherein retroreflectors 114 are disposed along a perimeter of area 110. In some embodiments, light source 300 is disposed in area 110. In some embodiments, light source 300 is disposed outside of area 110.

Collecting spectroscopic data 328 over multiple open paths around area 110 includes making measurements with the spectrometer and the system of retro-reflectors.

Measuring atmospheric conditions along gas inflows and gas outflows of area 110 includes measuring the background values of the tracer gas coming into the computation domain as well as measuring the enhancements due to the leaks.

Subtracting the background for gas 140 from spectroscopic data 328 includes estimating the enhancement of the tracer gas over and above the background measurement. Time averaged background data (over 15 minute intervals) was used to obtain the average background concentration. This background value was subsequently subtracted from the downwind beams to obtain the average enhancement over a 15-minute period. It is contemplated that subtracting the background includes determining a lowest concentration of the selected gas in the open-path beams by finding the minimum value of all the data that has been collected during a 15-minute interval.

Time-resolved location and quantification of sources with the sparse array of line-of-sight integrated open-path measurements provided by the dual comb spectrometer involves an inversion technique. Spectroscopic measurement data is combined with model data in a least square framework to estimate and locate the leaks. A statistical inversion technique that is able to identify and quantify emission rates at multiple possible source locations, give a time series of observations and related covariance, an atmospheric transport model to relate the source and open-path measurements and estimates of temporal and spatial emission and background covariance.

Applying bootstrapping to spectroscopic data 328 includes a statistical method for accurately locating one or more point sources within a large area using distributed measurements of methane concentration and an atmospheric transport model. The method can be coupled with an atmospheric observing system that provides quasi-continuous monitoring of facilities. The source-attribution method uses a non-negative least-squares fitting technique to solve for methane flux at a series of prior locations, give a set of atmospheric observations and knowledge of atmospheric transport.

Applying zero minimum elimination to spectroscopic data 328 includes bootstrapping of model uncertainties in order to produce an empirical distribution of source strength for a given well site. Specifically, the empirical distribution is obtained by performing multiple atmospheric inversions using a set of resampled atmospheric measurements.

The method establishes a criterion by which well sites or facilities are identified as having non-zero methane emissions based on examination of the minimum value of an ensemble of inversions. A potential leak site is positively identified as a source of methane to the atmosphere if the empirical cumulative distribution of likely source strengths does not include zero flux. Similarly, a facility is identified as not leaking if the empirical cumulative distribution of likely source strengths does include zero. By defining a specific null value for each potential leak, this approach reduces the incidence of false positive leak identification. In an embodiment, the process includes continuously measuring an atmospheric concentration of gas 140 from gas source 130 along the open-path beams.

Moreover, clustering can include determining a location of spectrometer gas monitors 112 by K-Means cluster analysis and data mining. The clustering analysis partitions a large field of well pads into smaller clusters. The approach minimizes the within-cluster sum of squares to identify a set of clusters and to determine the optimum number and location for a network of spectrometers.

Further, performing orthogonal beam sampling can include disposing a pair of retroreflectors 114 of spectrometer gas monitor 100 relative to gas source 130 such that gas source 130 is interposed between the pair of retroreflectors 114. The orthogonal beam sampling allows for measuring the background concentration and for making the measurement process efficient.

Gas spectrometer monitor 100 and processes herein have numerous advantageous and beneficial properties. The dual comb spectrometer overcomes the limitations of single or sparse wavelength absorption of LIDAR approaches; it enables accurate correction of the baseline laser intensity, and simultaneous measurement of $CH_4$, $^{13}CH_4$, $H_2O$, other species (such as ethane and propane), temperature and pressure. It therefore reports, interference-free, true dry-air model fractions that account for variable water vapor dilution. With no instrument distortion and a near perfect wavelength axis, the technique is also drift- and calibration-free. The solution requires no operator involvement and is capable of integrating multiple point sources simultaneously.

The articles and processes herein are illustrated further by the following Example, which is non-limiting.

EXAMPLE

Advances in natural gas extraction technology have led to increased activity in production and other sectors, and as a consequence, an increased need for reliable monitoring of methane leaks to the atmosphere. Determining a location and size of a gas source is described in the Example in which is provided detecting one or more point gas sources of methane within a large area (4+km$^2$) using distributed measurements of methane concentration and an atmospheric transport model. The methodology applies a bootstrapping algorithm to determine whether the empirical distribution of possible source strengths for a given location excludes zero, thereby rejecting the null hypothesis that the source is not leaking. Synthetic data inversions are used with varying measurement density and varying levels of model-data mismatch. The determination includes non-zero minimum bootstrap method (NZMB) and decreases the incidence of false alarms, i.e., misidentifying a well site to be leaking, and offers increased leak detection and sizing capabilities over simple least-squares fitting technique. In the beam configuration described, 16 or more beams consistently detected 2 leaks in a field of 20 well sites. The NZMB technique offers increases confidence of leak detection in the natural gas supply chain.

Here, the method accurately locates one or more point gas sources of methane within a large area (4+km$^2$) using distributed measurements of methane concentration and an atmospheric transport model. This method can be coupled with an atmospheric observing system that provides quasi-continuous monitoring of facilities. The source-attribution method applies a non-negative least-squares fitting technique to solve for methane flux at a series of prior-known locations, given a set of atmospheric observations and knowledge of atmospheric transport. NZMB uses a bootstrapping of model uncertainties to produce an empirical distribution of source strength for a given well site. The empirical distribution is obtained by performing multiple atmospheric inversions (or least-squares fits) using a set of resampled atmospheric measurements. The NZMB method establishes a criterion by which well sites or facilities are identified as having non-zero methane emissions based on examination of the minimum value of an ensemble of inversions. That is, a potential leak site is positively identified as a source of methane to the atmosphere if the empirical cumulative distribution of likely source strengths (determined with a series of bootstrap operations) does not include zero flux. Similarly, a facility is identified as not leaking if the empirical cumulative distribution of likely source strengths does include zero (that is, the minimum value of all bootstrap operations is zero). By defining a specific null value for each potential leak, this approach reduces the incidence of false positive leak identification (the incorrect attribution of a methane source to a non-leaking facility or well).

NZMB is used in a series of synthetic data tests with an atmospheric measurement configuration composed of one long-range open-path laser situated in the center of a field of well sites, and a series of retroreflectors around the perimeter of the field to direct light back to a detector co-located with the laser. The concentration of trace gases along the beam path is determined from the species-specific absorption of light. For trace gas measurement over time concentrations can be compared across different wind conditions. The determination can include dual frequency-comb technology for atmospheric trace gas measurements over 2 km path lengths with high precision and stability.

The synthetic observation data is generated in a theoretical 2 km×2 km field containing 20 natural gas wells, 2 of which are leaking into the atmosphere at respective rates of 3E-5 and 4.5E-5 kg/s (considered to be very small leaks). We simulate measurements along a series of beams in a hub-and-spoke pattern, extending from a spectrometer in the middle of the domain to retroreflectors around the edge of the domain. Synthetic data (i.e. enhancements along the beam paths) are created using a plume model with idealized local meteorological observations. Temporal evolution of fluxes is not considered, and idealized meteorological conditions are not considered time dependent.

NZMB offers improved leak detection by comparing it with a non-bootstrap inversion. We test the effects of increasing measurement density (4, 8, 16, 32, and 64 beams) and effects of increasing model data mismatch (that is, "observation" noise arising from measurement, transport and other uncertainties). NZMB performance can be based on several metrics:

Leak identification success (location and size) rates under the same simulation conditions Leak identification success (location and size) under conditions of increasing model-data mismatch Leak identification success rates and solution convergence under scenarios of increasing measurement density (simulating an observing system with 4, 8, 16, 32, and 64 beams)

Leak identification success is a minimal occurrence of false positive source identification. With the above tests, NZMB method allows for leaks to be positively identified under scenarios of greater simulated noise, compared with the non-bootstrap method, and higher density of observations increases likelihood that the NZMB can positively identify leaks. The results of these tests demonstrate this system provides continuous monitoring of natural gas facilities for leaks and provides methane source locations and their approximate strengths.

Figure 13:
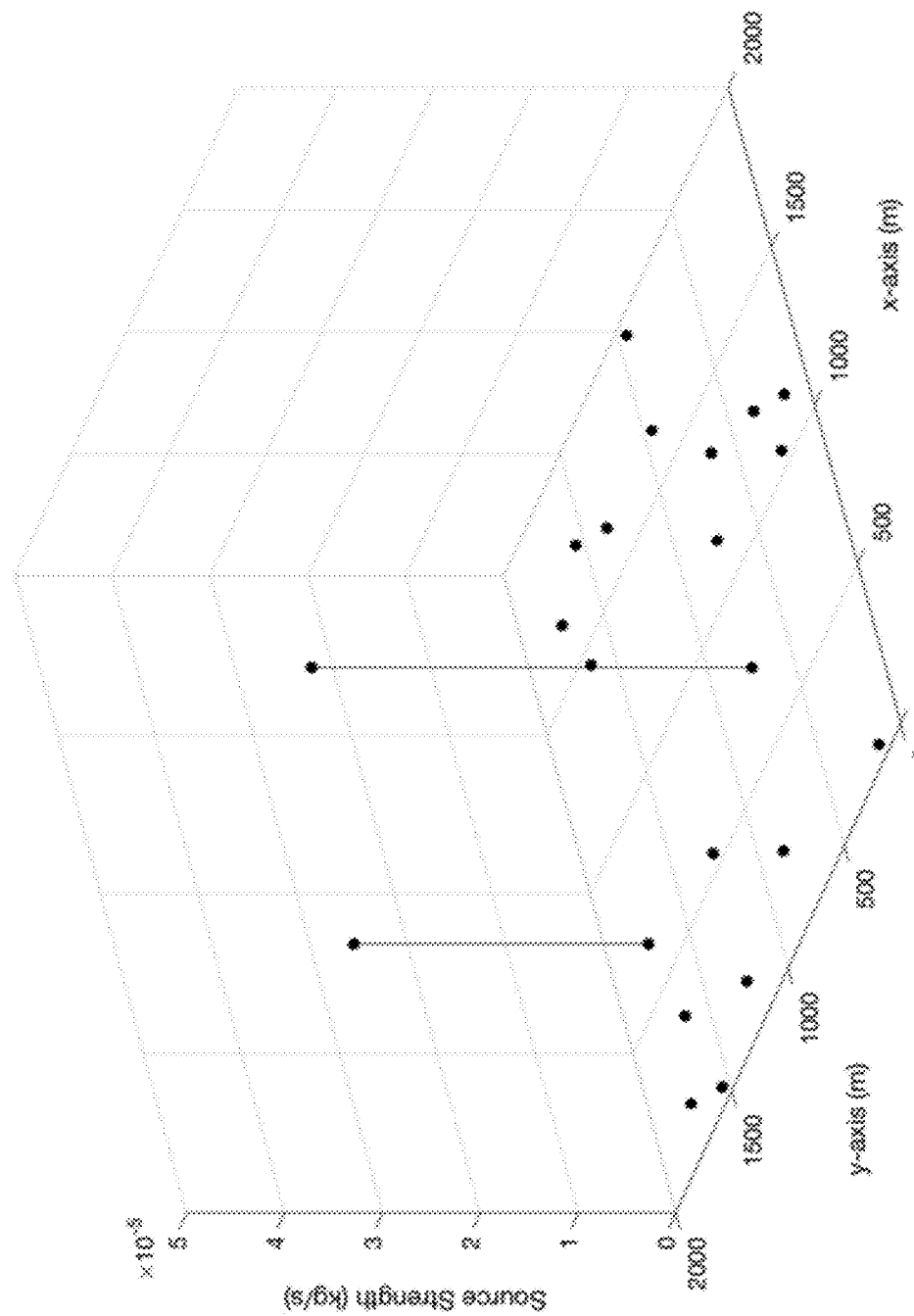
FIG. 13 shows a graph of source strength versus position.

We randomly distribute 20 possible leak source locations within a 2 km×2 km domain. This is a reasonable approximation of well density based on high-production regions of the western United States (average well density across the Marcellus and Haynesville shale gas plays are 3+wells km$^{-2}$). Of the 20 wells sites in the domain, we simulate a scenario in which 2 source locations are leaking. The "true" leak rate at well site number 6 is 4.5E-5 kg/s and the "true" source at well site number 19 has a rate of 3.0E-5 kg/s. The remaining 18 well sites are assigned "true" leak strengths of 0 kg/s (FIG. 13). The two "true" leak strengths tested here are roughly half the size of the smallest leaks previously determined in a survey of oil and natural gas well pads. We assume that the height above ground level of each leak is zero meters.

The meteorological data used to test the model represents an idealized scenario in which many wind directions and a variety of wind speeds occur during the sampling of each beam in the domain. Leak strengths are simulated to be constant through time, such that the time dimension of the meteorology need not be considered (we assume only that enough time has passed for all meteorological conditions to have occurred during the sampling each beam). The idealized meteorological field applies 216 unique wind conditions to all beams: three wind speeds (2 m/s, 3 m/s and 6 m/s) from 72 directions (from 5° to 360°, in 5° increments). The conditions represent a situation where, over a long period of time, many different wind conditions yield a variety of different measurements downwind of emissions.

Figure 14:
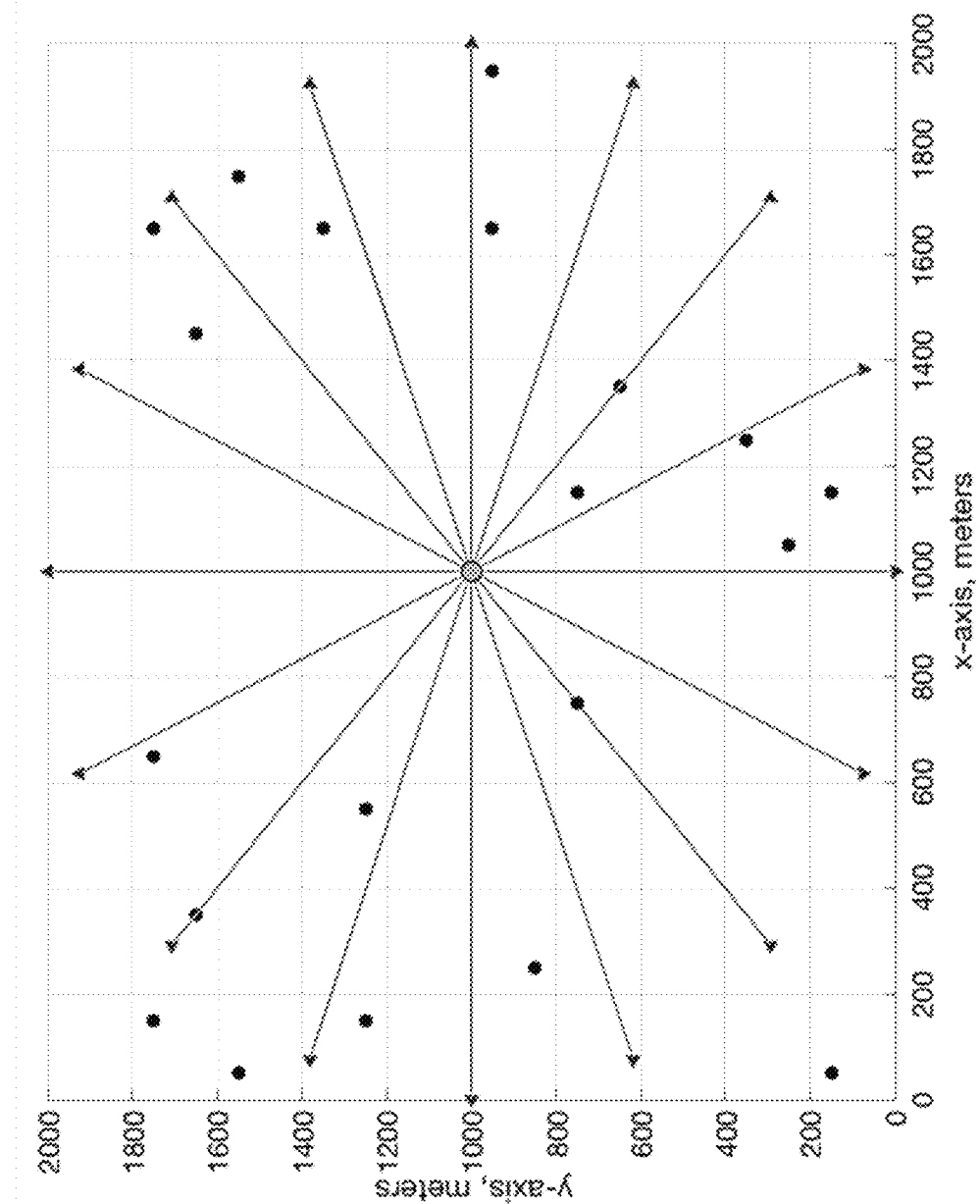
FIG. 14 shows a map view of an area with 20 gas source locations shown as black dots and 16 open-path beams shown as gray lines that extend from the spectrometer (circle at x=1000 m and y=1000 m) to retroreflectors (black triangles)

The synthetic atmospheric measurements are simulated based on an observing system composed of a dual frequency-comb spectrometer, a series of retroreflectors, and a light detector that is collocated with the spectrometer. The spectrometer is located in the center of the domain, at x=1000 m and y=1000 m (FIG. 14). In the field, a measurement would be made by transmitting light from the spectrometer through open air at a discrete set of wavelengths where methane absorbs light. The light is transmitted in the direction of a retroreflector, which can be placed 1+km away. The retroreflector directs light back toward a detector co-located with the spectrometer. The amount of light that is absorbed by methane yields a direct measurement of the average mole fraction of methane along the open path from spectrometer to retroreflector.

A beam is the path between the spectrometer-detector system and a retroreflector. Configurations of 4, 8, 16, 32, and 64 beams per spectrometer-detector system are tested. In all beam configurations, retroreflectors are placed at an equal distance (1000 m) from the spectrometer and at equal distances from neighboring retroreflectors (e.g., FIG. 14). The hub-and-spoke beam configuration is a simple and repeatable pattern for which to compare different numbers of beams. The height of the spectrometer and retroreflectors is 3 m above ground level. FIG. 14 shows beams, beam end point locations (retroreflectors) and the spectrometer in a case with 16 beams.

True atmospheric methane concentrations are simulated by combining knowledge of atmospheric transport with knowledge of true sources and measurement (beam segment) locations. Neglecting influence of background methane concentrations, Equation 1 shows the relationship between fluxes and atmospheric concentrations:

$$c = x \ast (c/x)_{modeled} \qquad \text{Eq. 1}$$

Equation 1 shows the n×1 vector c: the atmospheric concentration of the constituent of interest at various points in space and or time, where n is the number of measurements (e.g. 8 beams by 216 meteorological conditions). The vector x is m×1 surface sources of the constituent (flux units), where the size of m is equal to the number of source flux locations (i.e. 20 well sites). The value $(c/x)_{modeled}$ is an influence function describing the relationship between source emissions and concentrations at observation points (spectrometer beams) under different meteorological conditions, as modeled using an atmospheric transport model. The matrix $(c/x)_{modeled}$ is commonly written as H.

To generate the synthetic measurement data, each beam path is discretized into 100 segments. For each unique wind condition, true source fluxes are combined with atmospheric transport to calculate atmospheric enhancements at each of the 100 points along the beam path. Enhancements due to leaks are calculated independently for each segment of a beam and subsequently averaged for each beam and for each wind condition. This value mimics the actual data output of the spectrometer, which measures the average concentration along the beam length.

The influence functions describing the relationships between each element of x and each segment of each beam path (e.g., FIG. 14), for each wind condition, H, are created using a Gaussian plume model. The plume model is parameterized with neutral stability conditions (Pasquill category D), using the Pasquill-Gifford sigmas. The synthetic data tests include a constant methane source to the atmosphere through time, and measurement frequency that is comparable to the travel time from source to measurement location. We create a vector of true atmospheric values, c, using Eq. 1.

Model-data mismatch is a difference between true atmospheric $CH_4$ concentration, c, and the simulated or measurable atmospheric $CH_4$ concentration. This difference is expected to be non-zero due to measurement uncertainty (sampling and instrumental error), transport uncertainty (imperfect knowledge of air flow between source and observation points), or representation error (e.g., the assumption that the measured segment of beam appropriately characterizes the atmospheric concentration at the time and space scales that it represents in the model). Uncertainty due to imperfectly known background concentration is part of model-data mismatch uncertainty here. We simulate progressively larger levels of model-data mismatch to identify differences in model capabilities to locate and size leaks between the NZMB and non-bootstrap methods.

To simulate different possible magnitudes of model-data mismatch, the true atmospheric concentrations, c, are perturbed with random Gaussian noise of a magnitude equal to the following values: 0.1, 0.2, 0.3, 0.4, 0.5, 1.0, 1.5, 2.0, 2.5, 3.0, 3.5, 4.0, 4.5, 5, 6, 7, 8, 9, and 10 ppb, over a 1 km path. Measurement noise alone is expected to be on the order of 3 ppb or lower for a 1 km path. A range of model-data mismatch values are tested with the expectation that both the NZMB and non-bootstrap models will locate and source leaks when lower model-data mismatch is added to the data. Each level of model-data mismatch is tested by perturbing the synthetic atmospheric observations with random Gaussian noise of mean 0 ppb and standard deviation equal to the model-data mismatch value. In Eq. 2, ε is a vector of measurement uncertainty corresponding to the vector, c. Both vectors are of length n (i=1, ..., n), where n is the number of observations. The vector y contains the synthetic observations, or the true atmospheric concentrations perturbed with measurement noise.

$$y_i = c_i + \varepsilon_i \qquad \text{Eq. 2}$$

We use a non-negative least-squares (NNLS) algorithm, which iteratively solves for the best-fit m×1 vector of fluxes, x, given an n×1 vector of synthetic data measurements, y, and an n×m matrix of influence functions, H. Given H and y, the NNLS algorithm attempts to solve the least squares problem for the vector x (i.e. methane emission rate at each of the 20 well sites):

$$Hx = y, \text{ subject to } x >= 0 \qquad \text{Eq. 3}$$

Uncertainties in x and y are not included in the NNLS fit; model-data mismatch is used only in generation of the synthetic observations, and not as a control on the solution for x. The NNLS algorithm not only returns the solution vector, x, but also Hx, an n×1 vector describing the expected atmospheric concentration given H and the solution for x.

The non-zero minimum bootstrap analysis is a statistical test of the null hypothesis that the source strength at a given well site is equal to 0 kg/s. That is, for each of m well sites:

$H_0$: $x_j = 0$ (j=1, ..., m)
$H_1$: $x_j > 0$ (j=1, ..., m)

Given that model-data mismatch uncertainty is not zero (i.e., there is uncertainty in the exact relationship between atmospheric observations and surface fluxes due to transport, measurement and other uncertainties), the NNLS fit of Hz to y may not be exact. We use the mismatch between Hz and y to create an empirical distribution function describing the confidence interval of the fit to the data, and to accept or reject the null hypothesis claim that we have enough evidence to claim that a particular source is not leaking. The model-data mismatch uncertainty has an un-biased Gaussian distribution.

The method for employing the bootstrap analysis includes solving for surface-to-atmosphere fluxes of $CH_4$, x, using NNLS. For each observation, $y_i$ (i=1, ..., n), we calculate the residual values from the fit to the NNLS solution:

$$\varepsilon_{Ri} = y_i - \hat{y}_i, \qquad \text{Eq. 4}$$

where $\hat{y}_i$ (i=1, ..., n) are the individual values in the vector Hx.

For each observation, $y_i$ (i=1, ..., n), we generate 1000 values with mean zero and standard deviation (following a Gaussian distribution) equal to $\varepsilon_{Ri}$, or the residuals of the fit of the NNLS solution to the atmospheric observations. That is, we generate 1000 new estimates of $y_i$ by sampling residuals of the fit to the atmospheric data, with replacement (that is, a given value can be sampled more than once), and adding that value to the observation to create $y_{bi}$. This step results in 1000 vectors $y_b$ (b denotes a bootstrapped value), or 1000 sets of observations $\{y_{b1}, \ldots, y_{bm}\}$, where $y_{bi} = y_i + \varepsilon_{bi}$.

We use NNLS to solve for x for each of the 1000 resampled sets of observations, yielding 1000 individual solutions for x. The final step in the NZMB method is to apply the non-zero-minimum criterion to the 1000 bootstrap solutions for each member of x. For each possible source location (each of the 20 well sites in FIG. 13), the minimum value from the 1000-member bootstrap analysis is obtained. The non-zero-minimum criterion states that if the minimum bootstrap value for a given well location is 0 kg/s, then the source location is classified as having a leak rate of 0 kg/s (i.e. no leak). In essence, what this criterion establishes, is whether or not 0 is included in the empirical cumulative distribution function described by the 1000 solutions for each well site in x. If zero is included in this distribution, then the null hypothesis (x=0) cannot be rejected. Conversely, if 0 is not included in the empirical cumulative distribution function for a given well site ($x_j$), then the null hypothesis can be rejected and it can reasonably be assumed that that well site is leaking. We use a large number of bootstrap members (1000) to ensure that the law of large numbers is met, and that the empirical cumulative distribution function is a close enough approximation of the true cumulative distribution function.

After having identified which source locations are non-zero sources to the atmosphere (i.e. leaking), the mean leak strength is estimated as the mean of the 1000 bootstrap solutions for that source location. Uncertainty in the strength of the true leak is calculated as the standard deviation of the 1000 bootstrap solutions at the true leak location.

This method includes low computational cost over the non-bootstrap NNLS approach because additional runs of the transport model are not required, only additional inversions using resampling of the observations. The NZMB approach has the benefit of reducing false positive solutions while also gathering information regarding the probability distribution of the results.

Figure 15:
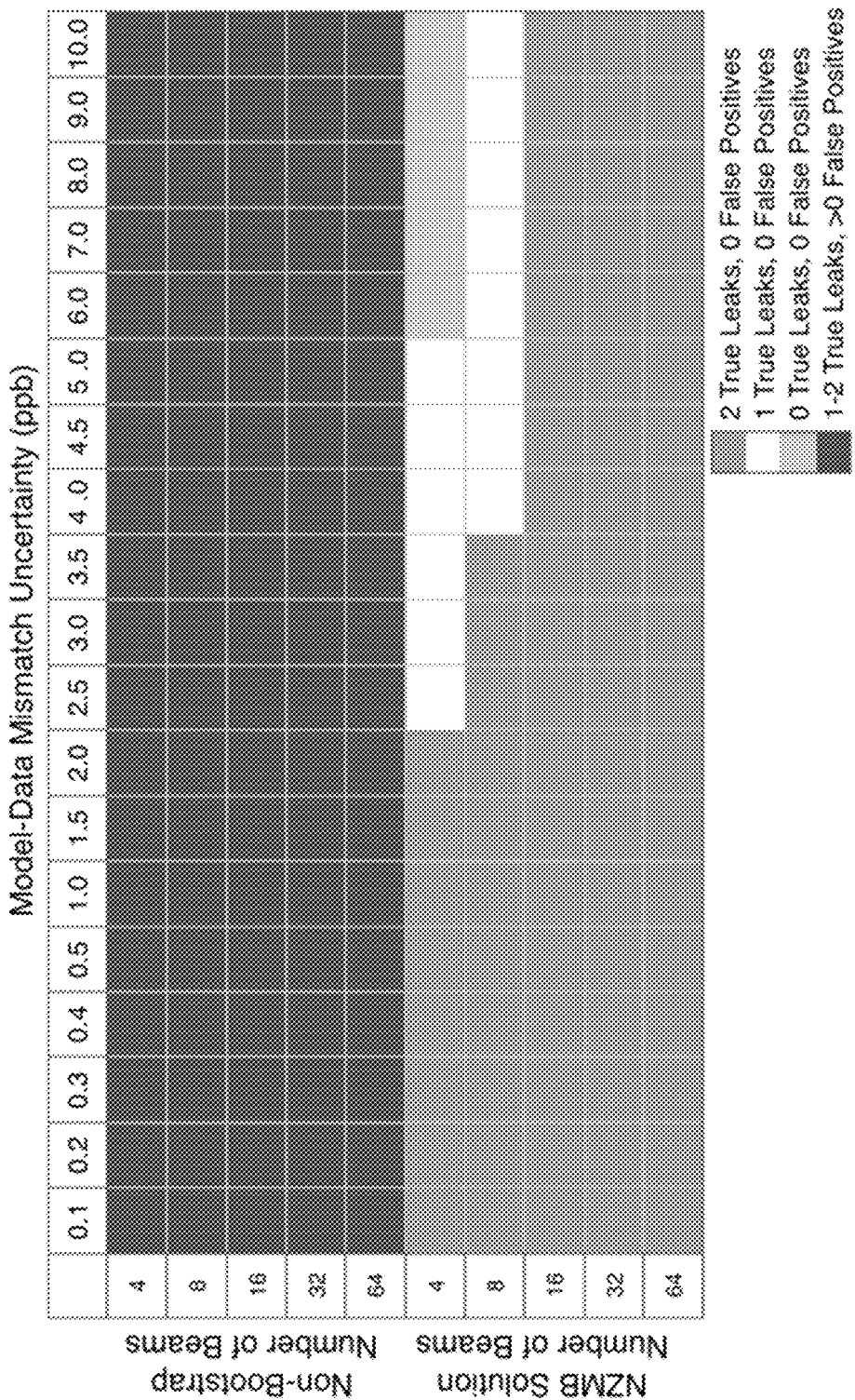
FIG. 15 shows results for synthetic tests in which the top five rows include non-bootstrap inversions, and the bottom 5 rows include NZMB inversions.

We calculate solutions for x using NNLS in a single solution without a bootstrap approach for each set of beam configurations and for each model-data mismatch scenario. FIG. 15 summarizes the findings of each test by categorizing the results into 4 outcomes: 2 true leaks found with no false positives, 1 true leak found with no false positives, 0 true leaks found with no false positives, and 1-2 true leaks found with 1 or more false positive. We find that, of the 5 different beam configurations, all result in false positive source locations under every model-data mismatch scenario. That is, even with very low model-data mismatch (0.1 ppb), and 64 beam measurement locations, the non-bootstrap method fails to positively identify true leak sources without also generating false positive results (i.e., non-zero solutions are found for source locations where no true leak exists).

FIG. 15 also shows results of tests that used the NZMB method for locating leaks. The results of these tests show much increased success in leak detection compared with the non-bootstrap tests. Indeed, none of the NZMB tests resulted in the occurrence of a false-positive leak location, and only tests with low numbers of beams (4 and 8 beam cases) failed to find both of the true leaks. The 4-beam case resulted in positive identification of both leaks up to a model-data mismatch threshold of 2 ppb, above which 1 true leak was found. One leak was consistently found up to a threshold of 5 ppb, and above 5 ppb model data mismatch no true leaks were identified (but no false positives were generated). The 8-beam case resulted in accurate location of both true leaks up to a model-data mismatch threshold of 3.5 ppb, above which 1 true leak was found (with no false positives). One leak was consistently found up to the maximum testing point of 10 ppb. In order to consistently locate both true leaks with no false positive results under all model-data mismatch scenarios, 16 or more beams were needed.

Figure 16:
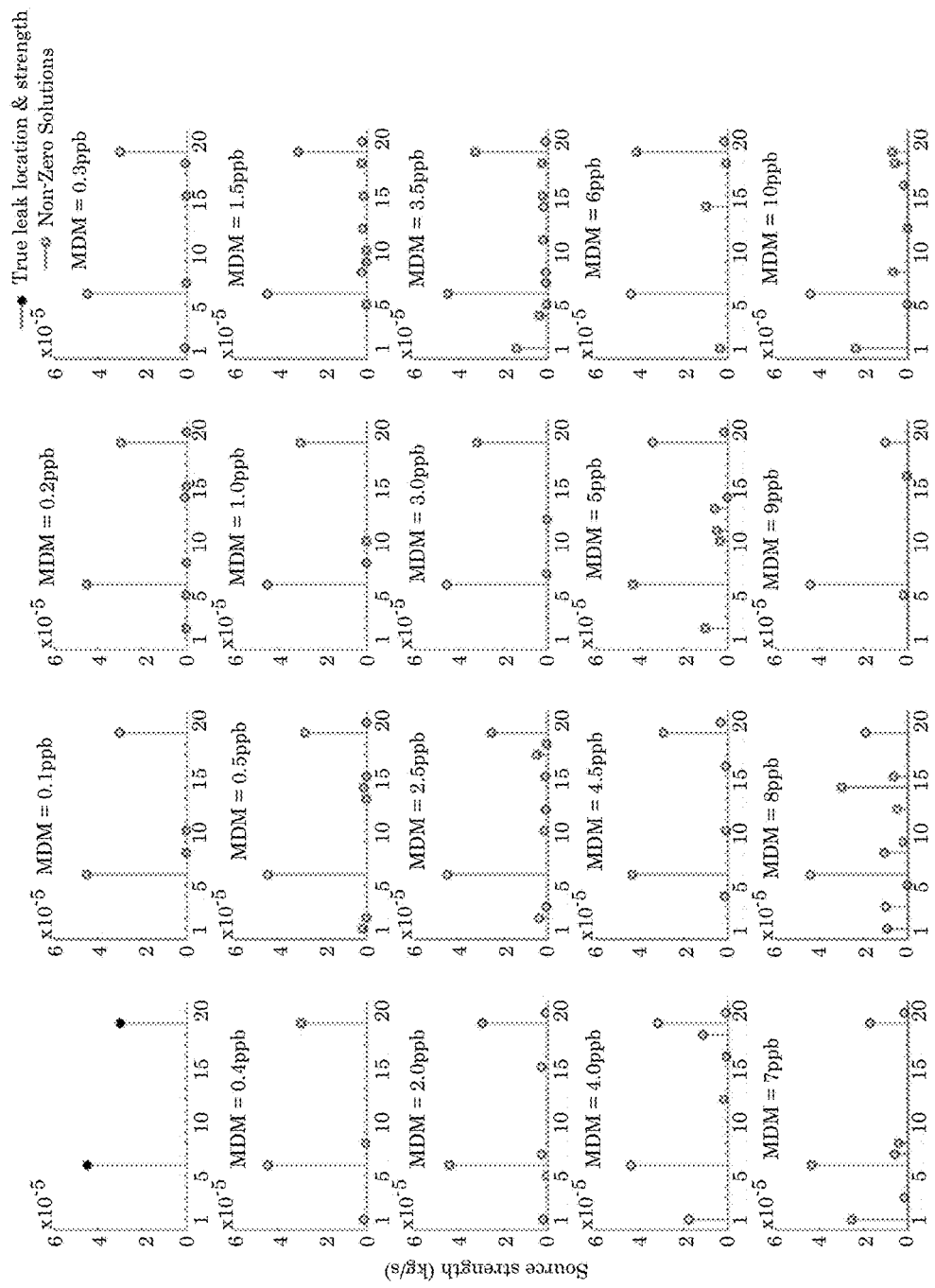
FIG. 16 shows in top left panel well site numbers (x-axis) and leak rates (y-axis), and other panels show leak rate (y-axis) at each well site (x-axis) from non-bootstrap least squares fit to synthetic observations perturbed with model-data mismatch (MDM) noise shown, wherein open circles show locations and strengths of all non-zero solutions.
Figure 17:
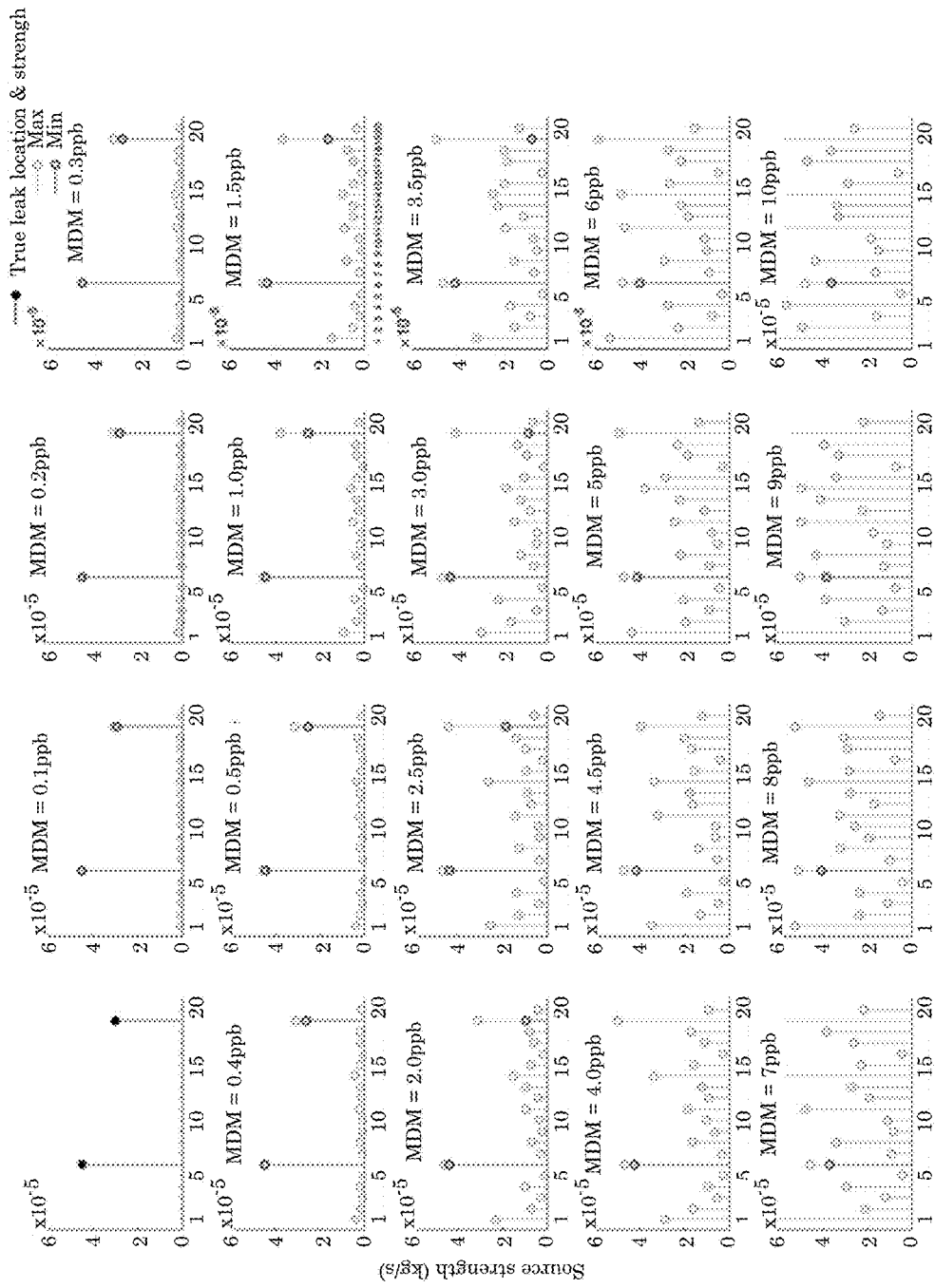
FIG. 17 shows in top left panel well site numbers (x-axis) and leak rates (y-axis), and other panels show NZMB results (y-axis) for each well site location (x-axis) with synthetic observations perturbed with MDM noise shown, for the 8-beam case, wherein light gray (black) open circles show locations and strengths of the maximum (minimum) of 1000 bootstrap operations.
Figure 18:
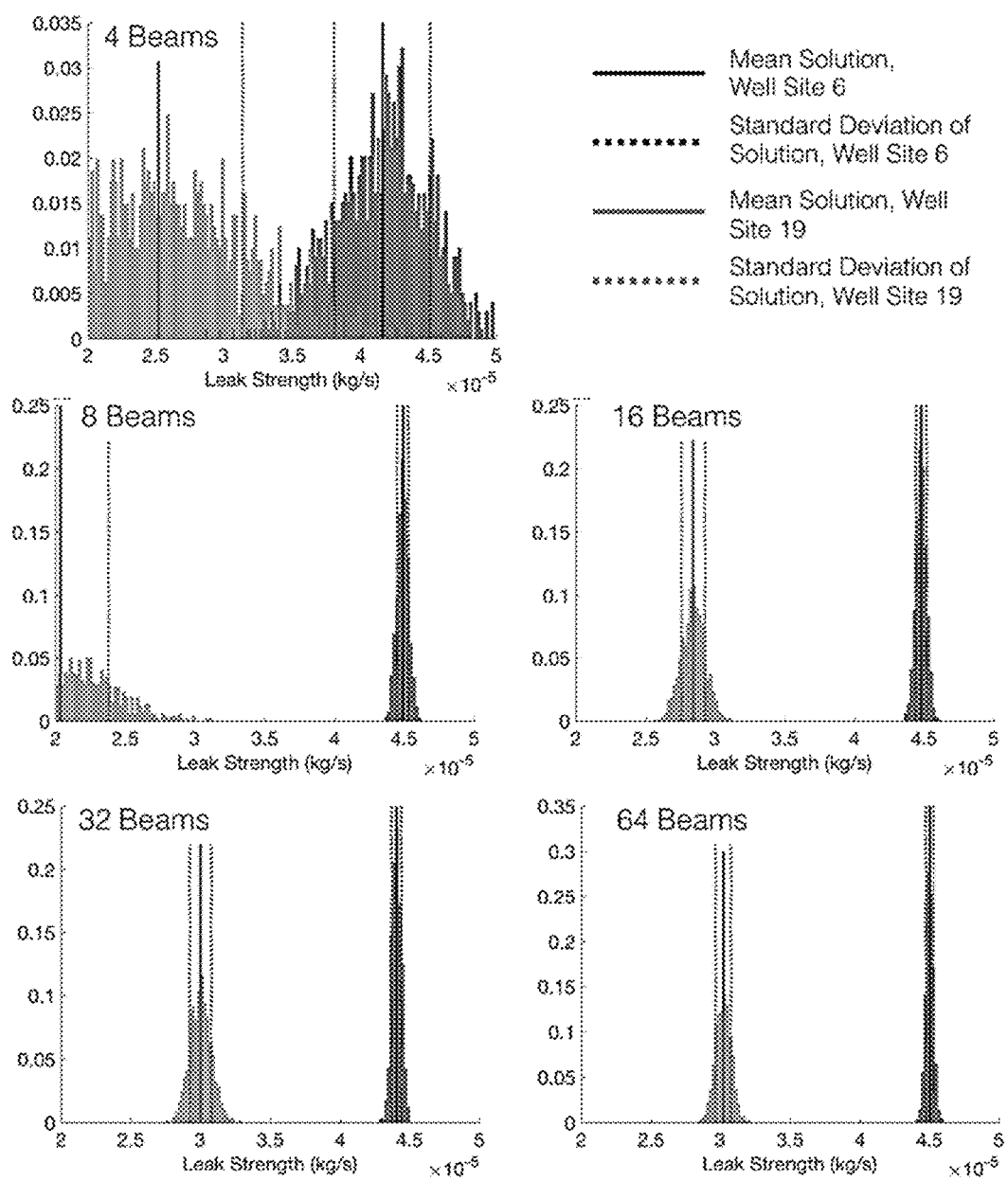
FIG. 18 shows graphs of frequency versus gas source strength with mean±1 standard deviation shown with vertical lines for well site 6 (black) and well site 19 (gray) for each beam configuration and with 2 ppb model-data mismatch uncertainty.

The results for the 8-beam NNLS without bootstrap and the NNLS with NZMB cases are shown in FIG. 16 and FIG. 17. FIG. 18 shows that with very low model-data mismatch noise (0.1 ppb) well sites other than the 2 true leak locations are erroneously identified as sources of methane to the atmosphere by the non-bootstrap model. By contrast, no leaks are identified outside of the locations of the two true leaks in the NZMB case shown in FIG. 17. Above a model-data mismatch threshold of 4 ppb, only one of two true leaks are found in the 8-beam case. As FIG. 3 shows, 16 or more beams are necessary to consistently find both true leaks at higher thresholds of model-data mismatch uncertainty, given the hub-and-spoke beam placement scheme tested here. More complex placement of beams (for example placing beams closer to known well sites) would likely result in even better ability to locate leaks with fewer beams.

Results here show success in leak location with zero incidence of false positive leak detections. Following successful identification of leak locations with the NZMB method, leak sizes can be estimated using the statistical distribution of bootstrap operations. FIG. 17 shows the maximum and minimum values of 1000 bootstrap operations for each model-data mismatch test case for the 8-beam configuration. At low levels of model-data mismatch uncertainty (e.g. 0.1-0.5 ppb), the maximum and minimum solutions bound a small range that is close to the true leak strength. As higher levels of model-data mismatch noise are added to observations, the maximum and minimum values diverge. In most cases, as the maximum and minimum solutions diverge, they include within their bounds the true leak strength. We use the mean and standard deviation of 1000 operations to estimate leak strength and its uncertainty.

All beam cases (even the 4-beam case) correctly identify that both well sites 6 and 19 are emitting methane when model-data mismatch is 2 ppb or lower (FIG. 15). At that level of model-data mismatch, higher numbers of beams and observations tend to lead to lower standard deviation around the mean estimated leak strength and a more accurate estimate of true leak strength (see Table). An exception is at well site 19, where the 8-beam case did not perform as well as the 4-beam case. Both cases may be inadequate for accurately sizing leaks and that 16 beams can be involved in a dense field of wells such as is tested here. The failure of the 8-beam case to accurately predict the leak rate at well site 19 is also evident from histograms of all bootstrap operations and is shown for each beam case with model-data mismatch of 2 ppb in FIG. 18.

TABLE

| Number of Beams | Well Site 6 Mean Strength | Leak One 1 s. d. | Well Site 19 Mean Strength | Leak Two 1 s. d. |
|---|---|---|---|---|
| 4 | 4.2E−5 kg/s | 0.4E−5 kg/s | 2.5E−5 kg/s | 0.6E−5 kg/s |

TABLE-continued

| Number of Beams | Well Site 6 Mean Strength | Leak One 1 s. d. | Well Site 19 Mean Strength | Leak Two 1 s. d. |
|---|---|---|---|---|
| 8 | 4.5E−5 kg/s | 0.4E−6 kg/s | 2.0E−5 kg/s | 0.3E−5 kg/s |
| 16 | 4.5E−5 kg/s | 0.4E−6 kg/s | 2.8E−5 kg/s | 0.9E−6 kg/s |
| 32 | 4.4E−5 kg/s | 0.3E−6 kg/s | 3.0E−5 kg/s | 0.8E−6 kg/s |
| 64 | 4.5E−5 kg/s | 0.3E−6 kg/s | 3.0E−5 kg/s | 0.6E−6 kg/s |

True Leak: 4.5E−5 kg/s
True Leak: 3.0E−5 kg/s

Figure 19:
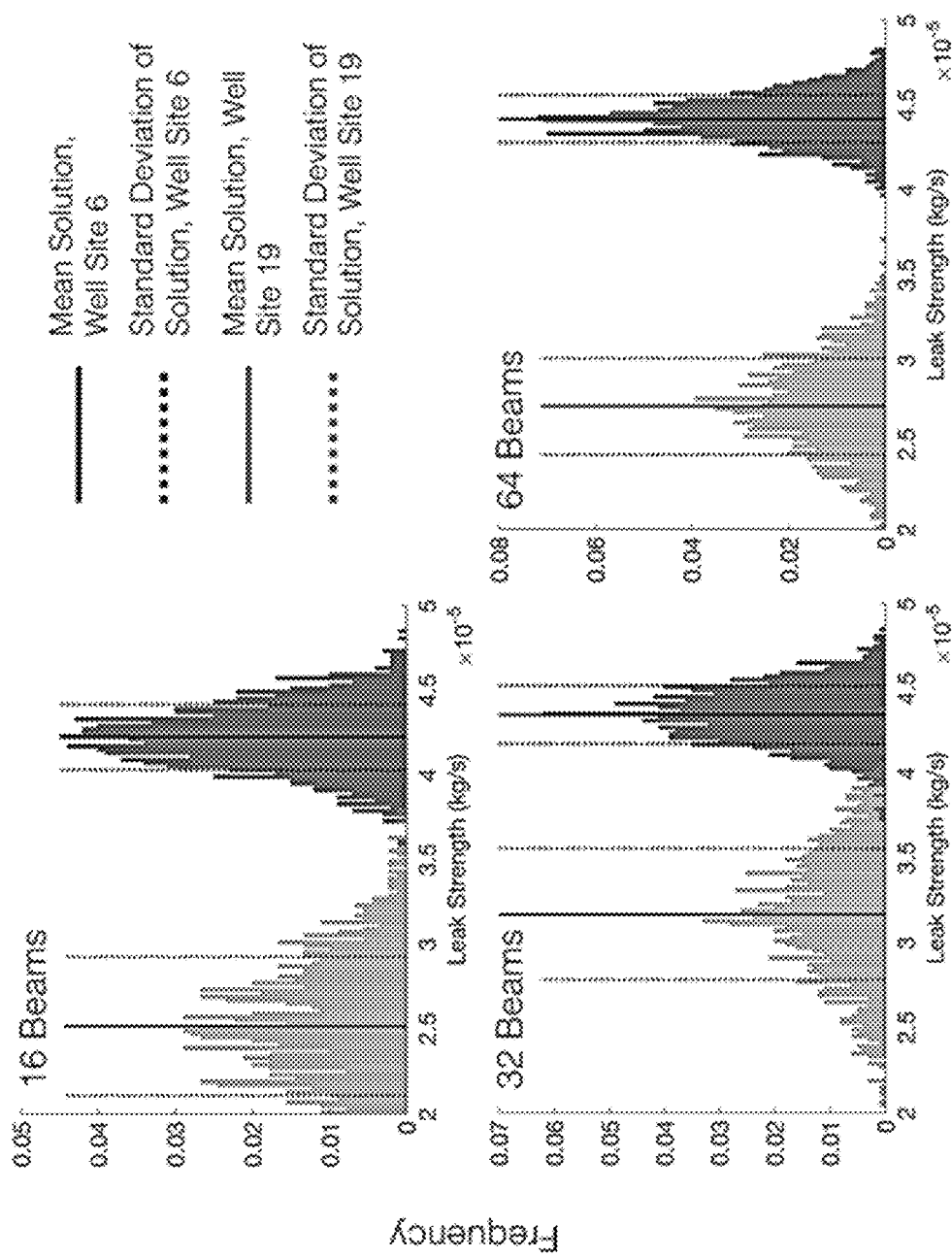
FIG. 19 shows graphs of frequency versus gas source strength with mean±1 standard deviation shown with vertical lines for well site 6 (black) and well site 19 (gray) for 16, 32, and 64 beam configurations and with 10 ppb model-data mismatch uncertainty.

Histograms of the results for the 16, 32 and 64 beam cases with 10 ppb model-data mismatch are shown in FIG. 19. With very high model-data mismatch uncertainty, the hub-and-spoke configuration of between 16-64 beams locate and estimate the size of leaks from the gas source within reasonable bounds of uncertainty.

The gas spectrometer monitor locates and sizes leaks of methane in a field of natural gas production facilities without incidence of false positive leak detection in contrast to tests without the NZMB. In the non-bootstrap tests, all cases resulted in false positive solutions (see, e.g., FIG. 15). NZMB correctly identifies two leaks of strength 3.0E-5 and 4.5E-5 kg/s with 4 or more beams monitoring 20 wells in a 4 km² area, with 2 ppb model-data mismatch uncertainty. NZMB finds both leaks with 16 or more beams with at least 10 ppb model-data mismatch uncertainty. Notably, NZMB locates and sizes both leaks with no false positive results.

Determination of leak strength was successful to within 25% (and all but a few cases well below 10%) for all cases with 16 or more beams, using NZMB.

Embodiments of the subject matter and the operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more computers executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, workstations, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic; magneto-optical disks, optical disks, USB drives, and so on. However, a computer need not have such devices. Moreover, a computer can be embedded in another device, e.g., a mobile telephone, a personal digital assistant (PDA), a microwave oven, mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The central processing unit and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks). Such interconnects may involve electrical cabling, fiber optics, or be wireless connections.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for determining a location and size of a gas source within an area with a spectrometer gas monitor, the process comprising:
    performing fence line monitoring of the area with the spectrometer gas monitor;
    collecting spectroscopic data over multiple open paths around the area with the spectrometer gas monitor;
    measuring atmospheric conditions along gas inflows and gas outflows of the area;
    subtracting a background value of a concentration of a selected gas from the spectroscopic data;
    applying a boundary constraint to the spectroscopic data;
    determining an atmospheric concentration of air entering the area;
    applying bootstrapping to the spectroscopic data;
    applying zero minimum elimination to the spectroscopic data; and
    producing inversion data from the spectroscopic data to determine the location and size of the gas source within the area.

2. The process of claim 1, further comprising:
    arranging a plurality of spectrometer gas monitors by clustering when the area is larger than 1 km$^2$.

3. The process of claim 1, further comprising:
    performing orthogonal beam sampling to constrain atmospheric conditions upwind and downwind of the area.

4. The process of claim 1, wherein the spectrometer gas monitor comprises:
    a light source that provides source light that propagate in the area as a plurality of open-path beams;
    a plurality of retroreflectors in optical communication with the light source and that receives the source light and reflects the source light as reflected light; and
    a detector that detects the reflected light.

5. The process of claim 4, wherein the source light comprises a source frequency comb that comprises comb teeth that comprise a first intensity, and the reflected light comprises a reflected frequency comb that comprises first comb teeth that comprise a second intensity such that a difference in intensity of the first intensity and the second intensity occurs due to absorption of source light.

6. The process of claim 5, wherein performing fence line monitoring comprises:
    encapsulating the area with a beam umbrella comprising open-path beams comprising the source light from the spectrometer gas monitor, wherein retroreflectors are disposed along a perimeter of the area.

7. The process of claim 6, wherein the light source is disposed in the area.

8. The process of claim 6, wherein the light source is disposed outside of the area.

9. The process of claim 6, further comprising:
    continuously measuring an atmospheric concentration of the selected gas from the gas source along the open-path beams.

10. The process of claim 9, wherein subtracting the background value comprises:
    determining a lowest concentration of the selected gas in the open path beams.

11. The process of claim 10, wherein applying the boundary constraint comprises:
    determining a concentration of the selected gas outside of the area.

12. The process of claim 11, wherein applying bootstrapping comprises:
    determining a surface-to-atmosphere flux of the selected gas.

13. The process of claim 2, wherein clustering comprises:
    determining a location of the spectrometer gas monitors.

14. The process of claim 3, wherein performing orthogonal beam sampling comprises:
    disposing a pair of retroreflectors of the spectrometer gas monitor relative to the gas source such that the gas source is interposed between the pair of retroreflectors.

15. A computer-implemented method, comprising:
    performing fence line monitoring of an area comprising a gas source that comprises a selected gas;
    collecting spectroscopic data of the selected gas over multiple open-paths around the area;
    measuring atmospheric conditions along gas inflows and gas outflows of the area;
    subtracting a background value of a concentration of the selected gas from the spectroscopic applying a boundary constraint to the spectroscopic data;
    determining an atmospheric concentration of air entering the area;
    applying bootstrapping to the spectroscopic data;
    applying zero minimum elimination to the spectroscopic data; and
    producing inversion data from the spectroscopic data to determine the location and size of the gas source within the area.

16. A system comprising:
    one or more computers configured to perform operations, the operations comprising:
        performing fence line monitoring of an area comprising a gas source that comprises a selected gas;
        collecting spectroscopic data of the selected gas over multiple open-paths around the area;
        measuring atmospheric conditions along gas inflows and gas outflows of the area;
        subtracting a value of a concentration of the selected gas from the spectroscopic data;
        applying a boundary constraint to the spectroscopic data;
        determining an atmospheric concentration of air entering the area;
        applying bootstrapping to the spectroscopic data;
        applying zero minimum elimination to the spectroscopic data; and
        producing inversion data from the spectroscopic data to determine the location and size of the gas source within the area.

17. A computer-readable medium having instructions stored thereon,
    which, when executed by a processor, cause the processor to perform operations comprising:

performing fence line monitoring of an area comprising a gas source that comprises a selected gas;

collecting spectroscopic data of the selected gas over multiple open-paths around the area;

measuring atmospheric conditions along gas inflows and gas outflows of the area;

subtracting a value of a concentration of the selected gas from the spectroscopic data;

applying a boundary constraint to the spectroscopic data;

determining an atmospheric concentration of air entering the area;

applying bootstrapping to the spectroscopic data;

applying zero minimum elimination to the spectroscopic data; and producing inversion data from the spectroscopic data to determine the location and size of the gas source within the area.

\* \* \* \* \*